United States Patent [19]

Kaplan

[11] 4,438,130
[45] Mar. 20, 1984

[54] ANALGESIC 1-OXA-, AZA- AND THIA-SPIROCYCLIC COMPOUNDS

[75] Inventor: Lester J. Kaplan, Kalamazoo, Mich.

[73] Assignee: The Upjohn Company, Kalamazoo, Mich.

[21] Appl. No.: 390,462

[22] Filed: Jun. 21, 1982

Related U.S. Application Data

[63] Continuation-in-part of Ser. No. 320,635, Nov. 12, 1981, abandoned.

[51] Int. Cl.³ ............... A61K 31/34; A61K 31/35; C07D 307/94; C07D 311/96
[52] U.S. Cl. ............... 424/274; 260/330.3; 260/330.9; 424/267; 424/275; 424/283; 424/285; 546/15; 548/407; 549/13; 549/77; 549/331
[58] Field of Search ............ 260/330.3, 330.9; 549/13, 77, 331; 548/407; 546/15; 424/274, 275, 283, 285, 267

[56] References Cited

U.S. PATENT DOCUMENTS

| | | | |
|---|---|---|---|
| 4,065,573 | 12/1977 | Lednicer | 424/278 |
| 4,098,904 | 7/1978 | Szmuszkovicz | 424/324 |
| 4,145,435 | 3/1979 | Szmuszkovicz | 424/274 |
| 4,212,878 | 7/1980 | Lednicer | 424/274 |

OTHER PUBLICATIONS

Backvall, Tetra Let., No. 2, (1978), pp. 163-166.
Wittekind et al., J. Het. Chem., vol. 4, (1967), pp. 143-145.
Hodjat et al., J. Het. Chem., vol. 9, (1972), pp. 1081-1086.
Eaton et al., J. Org. Chem., vol. 37, (1972), pp. 1947-1950.
Backvall, J. Org. Chem., vol. 44, (1979), pp. 1953-1957.
Lier et al., Helv. Chim. Acta., vol. 62, (1979), p. 96.
Jeremic, Chemical Abstracts, vol. 85, (1976), 123401u.
Ross, J. Amer. Chem. Soc., vol. 69, (1947), pp. 2982-2983.
Gillis et al., J. Org. Chem., vol. 28, (1963), pp. 1388-1390.
Leonard et al., J. Org. Chem., vol. 30, (1965), pp. 821-825.
Johnson et al., J. Org. Chem., vol. 35, (1970), pp. 622-626.

*Primary Examiner*—Richard Raymond
*Attorney, Agent, or Firm*—John T. Reynolds

[57] ABSTRACT

Mono-Oxa-, thiaspirocyclic-benzene-acetamide and -benzamide compounds of the formula

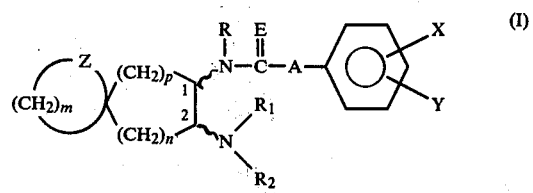

wherein p, n, m, A, E, R, $R_1$, $R_2$, X, Y and Z are as defined in the specification, e.g., ($\pm$)-($5\alpha,7\alpha,9\beta$)-3,4-dichloro-N-methyl-N-[7-(1-pyrrolidinyl)-1-oxaspiro[4.5]dec-8-yl]benzeneacetamide, and the pharmacologically acceptable salts thereof, are useful as analgesic compounds having low physical dependence liability, compared to morphine and methodone, and low dysphoria side effects. Some of these compounds have potent analgesic activity when administered orally, and some have low CNS sedative side effects. Pharmaceutical compositions and methods for using these compounds as analgesics are disclosed. Processes for preparing this class of compounds are also disclosed.

26 Claims, No Drawings

ANALGESIC 1-OXA-, AZA- AND THIA-SPIROCYCLIC COMPOUNDS

CROSS REFERENCE

This is a continuation-in-part of application Ser. No. 06/320,635, filed Nov. 12, 1981 now abandoned.

INTRODUCTION

This invention relates to 1-oxa-, thia- and aza-spirocyclicbenzene-acetamide and -benzamide compounds. More particularly this invention provides some new 1-oxa-, thia- and aza-spirocyclic-phenylacetamide and -benzamide compounds which have useful analgesic activity, low physical dependence and abuse liability properties, and little if any dysphoria inducing properties, or which compounds are useful as chemical intermediates to such useful compounds. Processes for their preparation are disclosed. Pharmaceutical compositions and methods of use are also disclosed.

BACKGROUND OF THE INVENTION

Szmuszkovicz U.S. Pat. No. 4,145,435 discloses some cis- and trans-N-(2-aminocycloaliphatic)-2-arylacetamide derivative compounds, e.g., N-[(N',N'-dimethylamino)cyclohexyl]-N-methyl-2-(4-bromophenyl-)acetamide and trans-N-methyl-N-[2-(1-pyrrolidinyl)-cyclohexyl]-2-(3,4-dichlorophenyl)acetamide, which have potent analgesic activity; the preferred compounds thereof have, in addition, only low to moderate apparent physical dependence liability compared to morphine and methadone. That Szmuszkovicz '435 patent also describes some prior art patent and publication background that may be of interest herein also.

Also, Szmuszkovicz U.S. Pat. No. 4,098,904 discloses some cis- and trans-N-(2-aminocycloaliphatic)benzamide compounds, e.g., N-methyl-N-(2-aminocycloaliphatic)benzamide compounds, e.g., N-methyl-N-[2-(1-pyrrolidinyl)cyclohexyl]-3,4-dichlorobenzamide which have potent analgesic activity, making them useful for relieving pain in warm blooded animals. That '904 patent also discloses background patents and publications which may be of interest herein.

Lednicer U.S. Pat. No. 4,212,878, discloses some N-[(1-amino-4-(mono- or di-oxygen-group-substituted)-cyclohexyl)methyl]benzene-acetamide derivatives, e.g., 2-(3,4-dichlorophenyl)-N[[8-(1-pyrrolidinyl)-1,4-dioxaspiro[4.5]dec-8-yl]methyl]acetamide, which also have analgesic drug properties with lower physical dependence liability characteristics than morphine or methadone. That Lednicer patent also refers to what is now Lednicer U.S. Pat. No. 4,065,573 which discloses some 4-amino-4-phenylcyclohexanoneketal compounds, e.g., 4-(m-hydroxyphenyl)-4-(dimethylamino)-cyclohexanone ethylene ketal and 4-(m-hydroxyphenyl)-4-(m-butylmethylamino)cyclohexanone ethylene ketal, which are useful for relieving pain in animals, some of which compounds exhibit narcotic antagonist activity.

A recently filed U.S. application, Ser. No. 06/252,535, filed Apr. 9, 1981, now U.S. Pat. No. 4,360,531, discloses some N-[2-amino-(oxy-group-substituted cycloaliphatic)]phenylacetamide and -benzamide compounds, e.g., trans-3,4-dichloro-N-methyl-[7-(1-pyrrolidinyl)-1,4-dioxaspiro[4.5]-dec-8-yl]benzamide, and salts thereof, as analgesic compounds having low apparent physical dependence liability properties.

Also, recently filed U.S. application Ser. No. 06/252,536, filed Apr. 9, 1981, now U.S. Pat. No. 4,359,476, discloses some N-2-amino-adjacently-oxy-substituted-cycloaliphatic-phenylacetamide and -benzamide compounds, e.g., cis- and trans-4-bromo-N-[3-methoxy-2-(1-pyrrolidinyl)cyclohexyl]-N-methylbenzamide, and cis- and trans-3,4-dichloro-N-methyl-N-[7-(1-pyrrolidinyl)-1,4-dioxaspiro[4.5]-dec-6-yl]benzamide, and salts thereof, as analgesic compounds having low apparent physical dependence liability properties.

Representative compounds of some of the above types have been or are being studied in advanced animal drug studies. Some concern has been expressed about possible dysphoric side effects of such compounds when used as analgesic drugs. Those skilled in the art continue to search for new and more potent and otherwise advantageous analgesic compounds.

OBJECTS OF THE INVENTION

It is an object of this invention to provide some new spiromono-oxy, thia- and aza ring-2-aminocyclohexyl-benzeneacetamide and -benzamide compounds which are useful as analgesic compounds or as chemical intermediates to analgesic compounds.

It is a further object of this invention to provide new compounds of the above type which have more potent analgesic properties when administered by either the oral, subcutaneous or other parenteral route, only low to moderate physical dependence liability, and hopefully also, less dysphoria inducing properties than prior known analgesic compounds.

Other objects, aspects and advantages of this invention will become apparent from reading the remaining specification and claims which follow.

SUMMARY OF THE INVENTION

Briefly, this invention provides some new, more potent spiromono-oxy-, thia- and -aza ring-2-aminocyclohexyl benzeneacetamide and benzamide compounds, e.g., ($\pm$)-5$\alpha$,7$\alpha$,8$\beta$-3,4-dichloro-N-methyl-N-[7-(1-pyrrolidinyl)-1-oxaspiro[4.5]dec-8-yl]benzeneacetamide, and salts thereof, which have been found to have useful ranges of analgesic properties for use in valuable warm blooded animals, including humans, while also having low apparent physical dependence liability, reduced sedative and/or dysphoria inducing properties, and better analgesic activities when administered by either the oral or parenteral routes to the warm blooded animal or human patient in need of pain relieving treatment.

This invention also includes compounds of the above general type which may exhibit some analgesic activity of their own, but which are of some importance as chemical intermediates for the preparation of more advantageous analgesic drug compounds included herein. This invention also includes pharmaceutical compositions containing these compounds as an active analgesic component and the method of inducing analgesic activity in the animal patient, including humans, by administering one of these new compounds in an amount effective and sufficient to induce analgesic activity, regardless of origin of the pain, e.g., traumatic pain, bone pain, cancer pain, post-surgical pain, homotropic pain, menstrual pain, headache, and the like. This invention also relates to the use of these new compounds in pharmaceutical dosage unit forms, to be used, hopefully more advantageously, by the oral or parenteral administration route, for the relief of pain in valuable animals and human patients suffering pain. With more potent analgesic compounds, it should be possible to administer less of the compound to obtain a desired degree of relief from pain in the patient.

DETAILED DESCRIPTION OF THE INVENTION

More particularly, this invention provides some new N-(2-amino-substituted cyclohexyl)benzeneacetamide and -benzamide compounds having a new chemical structure I (See GENERAL CHEMICAL STRUCTURE sheets) featuring a new asymmetric carbon atom and a (spiro mono-oxa-, thia- or aza-ring structure substituted)-2-amino cyclohexylbenzene-acetamide or -benzamide structure, which are more analgesically potent, more active administered by the oral route, and otherwise more advantageous than prior known compounds.

In the compounds of formula I, the wavy line bonds indicate a cis or trans relationship of the two nitrogen-containing groups at positions 1 and 2 of the cycloaliphatic ring, p is a whole number integer 0, 1 or 2, and n is a whole number integer 1, 2, or 3, so that the resulting cycloaliphatic ring containing them has six (6) carbon atoms;

m is 3 or 4;

A is a single chemical bond (—), —$(CH_2)_q$— where q is a whole number integer 1 to 4 or —$CH(CH_3)$—;

X and Y are independently selected from the group consisting of hydrogen, a halogen having an atomic number of from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxyacylamino (—NHC(=O)$R_4$ wherein $R_4$ is hydrogen or $C_1$ to $C_2$-alkyl);

R is hydrogen or $C_1$ to $C_3$-alkyl;

$R_1$ and $R_2$, taken separately, are each hydrogen, $C_1$ to $C_3$-alkyl or allyl;

$R_1$ and $R_2$, taken together with the nitrogen to which they are bonded complete a ring selected from the group consisting of azetidinyl, pyrrolidinyl and piperidinyl;

E is oxygen or sulfur;

Z is selected from the group consisting of oxygen (—O—), —$NR_3$—, bivalent sulfur (—S—), sulfinyl (—S(O)—) and sulfonyl (—$S(O)_2$—);

$R_3$ is hydrogen, $C_1$ to $C_3$-alkyl, benzoyl, X and Y-ring substituted benzoyl

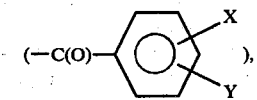

$C_2$ to $C_4$-alkanoyl (—C(O)—$C_1$ to $C_3$-alkyl); provided that when p is 2, n is 1, m is 3, A is (—$CH_2)_q$— where q is 1, R is methyl, $R_1$ and $R_2$ are taken together with the nitrogen to which they are bonded to complete a pyrrolidinyl ring, E is oxygen, Z is oxygen, and the relative stereochemistry is (5a, 7a, 8b), then X and Y taken together on the phenyl ring cannot be chlorine on the 2- and 4-positions of the phenyl ring.

Pharmacologically acceptable salts of such Formula I compounds are also part of this invention.

The compound excluded by the above proviso is (5a, 7a,8b)-2,4-dichloro-N-methyl-N-[7-(1-pyrrolidinyl)-1-oxaspiro[4.5]dec-8-yl]benzeneacetamide, and the pharmacologically acceptable salts thereof.

Thus, these new compounds contain a mono-oxy-, thia-, or aza-ring structure attached to the 4- or 5-position of the cyclohexyl ring and an asymmetric carbon atom at such position 4- or 5- which are not found in prior art compounds of which we are aware.

The compounds of Formula I or their acid addition salts in their crystalline state may sometimes be isolated from their reaction mixtures as solvates, i.e., with a discrete quantity of solvent, e.g., water, ethyl acetate, methanol, and the like, associated physically, and thus not affecting the chemical entity per se.

It will be recognized by those in the organic chemical art that the carbon atoms at positions 1 and 2 of the cyclohexyl ring of structure (I) to which nitrogens are bonded are asymmetrically substituted. Likewise, the cyclohexyl ring carbon atom to which the Z-ring is bonded is also asymmetrically substituted. Each of these three cyclohexyl carbon atoms can independently possess an R or S-configuration and thus a compound of the formula (I) may have as many as $2^3$ or 8 stereoisomers which comprise four pairs of enantiomers; each enantiomeric pair is termed a racemate. See, for example, J. B. Henderickson, D. J. Cram, and G. S. Hammond, Organic Chemistry, Third Edition, McGraw-Hill Book Company, New York, N.Y., 1970, pages 198–230, particularly pages 207, 208, 213, 215. Of the four racemates, two will have the nitrogen-containing groups at positions 1 and 2 of structure (I) in a trans orientation: that is, the groups will be on opposite sides of the plane of the cycloaliphatic ring; such compounds will be generally referred to in this specification as trans compounds and are meant to include both possible configurations of the third substituted ring carbon. The other two racemates will have the nitrogen-containing groups at positions 1 and 2 of structure (I) in a cis orientation: that is, the groups will be the on the same side of the cycloaliphatic ring; such compounds will be generally referred to in this specification as cis compounds and are meant to include both possible configurations of the third substituted ring carbon atom. The four racemates of structure (I) compounds each exist as a mixture of the two enantiomers or each enantiomer of each pair can be separated by conventional methods. This invention includes within its scope all enantiomeric and diastereomeric forms of the formula I compounds either in pure form or as mixtures of enantiomers or diastereomers. In General Chemical Structure Chart A and Schemes I through IX below, when a particular enantiomer or diastereomer or set of enantiomers or diastereomers is illustrated, the intent is only to convey relative stereochemistry. When it is desired to specify for a formula (I) compound the configuration of the other asymmetric centers relative to that of position 1, this is done according to the Chemical Abstracts Service publication, "Naming and Indexing of Chemical Substances for CHEMICAL ABSTRACTS during the Ninth Collective Period (1972-1976)," a reprint of Section IV (Selection of Index Names for Chemical Substances) from the CHEMICAL ABSTRACTS Volume 76 Index Guide. Accordingly, the relative stereochemistry of three asymmetric carbon atoms in the cycloaliphatic ring of formula I compounds is indicated by: (1) the arbitrary designation of 1α for the orientation of the substituent on (asymmetric) carbon atom number one; (2) the designation 2α or 2β when the substituent on (asymmetric) carbon atom number two is on the same or opposite side of the plane of the cycloaliphatic ring, respectively, relative to said $C_1$ substituent; and (3) the designation $x\alpha$ or $x\beta$ when the substituent on (asymmetric) carbon atoms number x is on the same or opposite side of the plane of the cycloaliphatic ring, respectively, relative to said $C_1$ substituent.

When the stereochemistry at carbon atom number x is unknown, the designation $x\xi$ (x Xi) is used to denote either a single epimer or a mixture of epimers at carbon atom x.

Two isomers which differ only in the stereochemistry at one asymmetric carbon atom of the cycloaliphatic ring are sometimes herein referred to as epimers.

If desired the formula I compounds of this invention can be resolved into their respective d- and l-optical isomers by methods known in the art. In this case, the optical resolution can be done by at least two different routes. The resolving agents by either route are any of the known resolving agents such as optically active camphorsulfonic acid, bis-o-toluyltartaric acid, tartaric acid, and diacetyl tartaric acid which are commercially available and which are commonly used for resolution of amines (bases), as for example in Organic Synthesis, Coll. Vol. V., p. 932 (1973), resolution of R-(+) and S-(−)-α-phenylethylamine with (−)-tartaric acid.

By the first method for resolving the compounds of this invention, for example, one of the aminoamide compounds can be converted into its optically active diastereomeric salts by reaction with an optically active acid—examples mentioned above—in a manner standard in the isomer resolution art. These diastereomeric salts can then be separated by conventional means such as differential crystallization. Diastereomeric salts have different crystallization properties, which are taken advantage of in this separation. On neutralization of each diastereomeric salt with aqueous base the corresponding optically active enantiomers of the free amino amide can be obtained, each of which can subsequently and separately be converted as hereinafter described in the examples to the desired acid addition salt.

By the second method, which in the case of some of these compounds is preferred, the formula I compounds can be made into their respective d- and l-isomers, by first resolving each cis- or trans-1,2-cycloaliphatic unsymmetrically substituted amino-alcohol or diamine into its respective d- or l-isomers by treatment with the resolving agent, crystallization, separation and regeneration of the respective trans-d-diamine, trans-l-diamine, or the cis-d-diamine and cis-l-diamine, and then reacting the respective resolved diamine starting material with the desired aracyl imidazole (III) or the acyl halide (IV) to form the respective cis or trans- d- or l- compound of Formula I, which can then be converted to any desired pharmaceutically acceptable acid addition salt by procedures exemplified hereinafter.

In the Formula I compounds, the halogens having atomic numbers of from 9 to 35 are fluorine, chlorine and bromine, the term "$C_1$ to $C_3$-alkyl" means methyl, ethyl, n-propyl and isopropyl.

A most significant subgroup of these Formula I compounds are those of formula Ia wherein p is 2, n is 1, m is 3, A is —$(CH_2)_q$— wherein q is 1, X and Y are each hydrogen or a halogen having an atomic number of from 9 to 35 in the 3-, 4-, or 2- or 3- and 4-positions, R is $C_1$ to $C_3$-alkyl, $R_1$ and $R_2$ are taken together with the nitrogen to which they are bonded to complete a ring selected from the group consisting of azetidinyl, pyrrolidinyl and piperidinyl, E is oxygen, and the pharmacologically acceptable salts thereof. Examples of this group of compounds include the cis- and trans-isomers of:

3,4-difluoro-N-methyl-N-[7-(1-azetidinyl)-1-oxaspiro[4.5]dec-8-yl]benzeneacetamide 4-bromo-N-ethyl-N-[7-(1-pyrrolidinyl)-1-oxaspiro[4.5]-dec-8-yl]benzeneacetamide 3-bromo-N-(n-propyl)-N-[7-(1-piperidinyl)-1-oxaspiro[4.5]dec-8-yl]benzeneacetamide 3,4-dichloro-N-methyl-N-[7-(1-pyrrolidinyl)-1-oxaspiro[4.5]dec-8-yl]benzeneacetamide, and the like, and the pharmacologically acceptable salts thereof.

In preliminary standard laboratory animal tests used to determine various properties associated with analgesia, a representative example of these new compounds has been shown to have a better analgesic potency than 2-(3,4-dichlorophenyl)-N-methyl-N-[2-(1-pyrrolidinyl)-cyclohexyl]acetamide, described and claimed in Szmuszkovicz, U.S. Pat. No. 4,145,435, referred to as the '435 patent compound herein. The lead compound of this invention $(\pm)$-$(5\alpha,7\alpha,8\beta)$-3,4-dichloro-N-methyl-N-[7-(1-pyrrolidinyl)-1-oxaspiro-[4.5]dec-8-yl]benzeneacetamide, referred to as the Example 1 compound herein has a better oral potency than the above '435 patent compound in standard laboratory animal tests. The ratio of sedative to analgesic activity of the Example 1 compound is about the same as that of the above '435 patent compound.

Thus, the compound of Example 1 is an analgesic drug compound lead of considerable importance. It is 2 to 4 times more potent than morphine by the subcutaneous route in standard laboratory animals and has good oral route activity. It is a member of this new group of 1,2-diamine derivative analgesic series of compounds which lack the typical physical dependence liability of morphine-like properties in mice, rats and monkeys. For example, chronic intravenous infusion of large doses of the Example 1 compound produces at most a low level of physical dependence. Because of these properties, the Example 1 compound was tested in rats at doses ranging from 0.032 to 0.32 mg/kg injection by self-administration methods to determine whether the compound caused any reinforcing properties compared to known analgesic drugs such as butorphanol, morphine, pentazocine and propoxyphene. In contrast to these known opiate compounds with agonist properties (which were actively self-administered by the rat test animals), the compound of Example 1 was not active at inducing the reinforcing side effect at the doses tested.

Examples of other compounds within the scope of this invention include:

(a) those wherein Z is —S—, —S(O)—, or —S(O)$_2$, such as:

3,4-dichloro-N-methyl-N-[7-(1-azetidinyl)-1-thiaspiro[4.5]dec-8-yl]benzeneacetamide, 4-bromo-N-ethyl-N-[7-(1-pyrrolidinyl)-1-thiaspiro[4.5]-dec-8-yl]benzeneacetamide, 1-oxide, 3-[3,4-difluoro-N-methyl-N-[8-(1-pyrrolidinyl)-1-thiaspiro[5.5]undec-9-yl]benzene]propionamide, 1,1-dioxide and the like.

(b) those wherein —Z— is —$NR_3$—, such as:

4-trifluoromethyl-1,N-dimethyl-N-[7-(1-pyrrolidinyl)-1-azaspiro[4.5]dec-8-yl]benzamide, 4-chloro-3-methoxy-N-ethyl-N-[8-(1-azetidinyl)-1-azaspiro[5.5]undec-9-yl]benzeneacetamide, 4-azido-N-methyl-N-[1-acetyl-7-(1-piperidinyl)-1-azaspiro[4.5]dec-8-yl]benzeneacetamide, and the like, and the pharmacologically acceptable salts of all of such compounds.

Some further more specifically structurally identified compounds of the above type included within this invention include:

(±)-(5α,7α,8β)-3,4-dichloro-N-methyl-[7-(1-pyrrolidinyl)-1-azaspiro[4.5]dec-8-yl]benzeneacetamide,
(±)-(5α,7α,8β)-3,4-dichloro-1,N-dimethyl-N-[7-(1-pyrrolidinyl)-1-azaspiro[4.5]dec-8-yl]benzeneacetamide,
(±)-(5α,7α,8β)-4-bromo-N-methyl-N-[7-(1-pyrrolidinyl)-1-azaspiro[4.5]dec-8-yl]benzamide,
(±)-(5α,7α,8β)-3,4-dichloro-N-methyl-N-[7-(1-pyrrolidinyl)-1-thiaspiro[4.5]dec-8-yl]benzamide,
(±)-(5α,7α,8β)-3,4-dichloro-N-methyl-N-[7-(1-pyrrolidinyl)-1-thiaspiro[4.5]dec-8-yl]benzeneacetamide, 1-oxide,
(±)-(5α,7α,8β)-3,4-dichloro-N-methyl-N-[7-(1-pyrrolidinyl)-1-thiaspiro[4.5]dec-8-yl]benzeneacetamide, 1,1-dioxide, and the pharmaceutically acceptable salts thereof.

In general, the new compounds of formula I can be prepared by reacting the selected 1,2-cycloaliphatic diamine of formula II, wherein the wavy line bonds, p, n, R, $R_1$, $R_2$, Z and m are as defined above with a suitable acyl source such as:

(1) the appropriate aracyl imidazole of formula III wherein q, E, X and Y are as defined above;

(2) an acyl halide of formula IV wherein M is chloride or bromide and q, E, X and Y are as defined above, in the presence of an acid scavenger such as triethylamine; or (3) the carboxylic acid of formula V where q, E, X and Y are as defined above, in the presence of a condensing agent, in an organic solvent for the reactants, preferably in an ether solvent such as diethyl ether or a cyclic ether solvent such as tetrahydrofuran (THF) or dioxane, or the like, until the compound of the invention is produced. Carbodiimides such as dicyclohexylcarbodiimide or diisopropylcarbodiimide can be used as condensing agents.

The reactants (II) and (III) or (II) and (IV) or (II) and (V) can be mixed in substantially equimolar proportions to effect formation of the desired product (I), but if one of the reactants (II), (III), (IV) and (V) is more expensive than the other, it is sometimes preferred to use a stoichiometric excess of the less expensive reactant to insure that substantially all of the more expensive reactant is consumed in the reactions. The reaction will proceed at ambient temperature for most combinations of reactants, but for some combinations of reactants, variations from the initial to final reaction conditions may vary between −25° C. and reflux temperature of the mixture depending on the reactivity of the reactants, the desired reaction time, the solvent being used, the molar proportions, and similar factors of concern to the chemist operating the process. When the new compound of this invention is to be one of formula (I) in which one or both of $R_1$ and $R_2$ are to be hydrogen, the amino-hydrogens in the $R_1$ and/or $R_2$ positions must first be protected by procedures known in the art, then the N-protected diamine reactant (IIa) wherein the wavy line bonds, R, Z, m, n and p are as defined for formula II and each "—H—Q" denotes that if present, an amino hydrogen has been protected from reaction, is reacted with the selected aracyl imidazole (III) or with the acyl halide (IV) or with the carboxylic acid (V) in the presence of a condensing agent to form the N-[2-(N-protected-amino)oxa or thia- or aza-group substituted cycloaliphatic]benzamide or -phenylacetamide, which is then treated to remove the N-protecting group to leave as product the desired N-[2-(amino)oxa, thia- or aza-group-substituted-cycloaliphatic]benzamide or -phenylacetamide.

Procedures for preparing the aracyl imidazoles (III) and acyl halide (IV) reactants used to form compounds of this invention are known in the art. See, for example, R. B. Wagner and H. D. Zook, SYNTHETIC ORGANIC CHEMISTRY, 1953, John Wiley and Sons, Chapter 17, p. 546 et seq. The aracyl imidazole can be prepared in situ by reacting carbonyldiimidazole with the acid of the formula (V) in an organic solvent. Carboxylic acids of the formula (V) are known in the art or are prepared by known methods.

Acid addition salts can be prepared by reacting a Formula I free base with a stoichiometric amount of an acid, such as hydrogen chloride, hydrogen bromide, hydrogen iodide, sulfuric acid, phosphoric acid, acetic acid, lactic acid, citric acid, succinic acid, benzoic acid, salicyclic acid, pamoic acid, cyclohexanesulfamic acid, methanesulfonic, naphthalenesulfonic, p-toluenesulfonic, maleic, fumaric, oxalic acids and the like. The reaction can be carried out in aqueous or organic liquid solvent, non-aqueous media such as diethyl ether, ethyl acetate, and the like. Non-aqueous media are preferred. Also, whereas oxalic acid and other equivalent acids can be used to produce the aminoamide product in a more easily handled solid form, e.g., in plant manufacturing isolation procedures, it would preferably not be used as a pharmaceutically acceptable salt form of the amino-amide product.

As indicated generally above, the amide bond of the compounds of formula I will be formed by the condensation of the selected diamine (II) with a carboxylic acid or acid derivative utilizing known methods. Preferred methods for this transformation are summarized in the following sets of conditions:

1. Diamine,

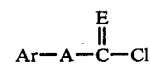

(where Ar denotes the

moiety),
tertiary amine or equivalent amine, tetrahydrofuran (THF) or diethyl ether (Et$_2$O) and 0° to reflux of the mixture.

2. Diamine,

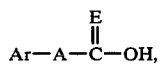

N,N'-carbonyldiimidazole, THF or Et$_2$O and 0° to reflux.

3. Diamine,

dicyclohexylcarbodiimide, THF or Et₂O and 0° to reflux.

4. Diamine,

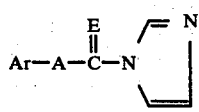

THF, or Et₂O and 0° to reflux.

5. Diamine,

tertiary amine, THF or Et₂O and 0° to reflux.

These methods require that all acidic hydrogens, which are not bonded to the nitrogen atom to be acylated, i.e., the phenolic or amino hydrogens, in the starting diamine and acid reactants be protected with a suitable protecting group.

Under certain circumstances it may be necessary to protect two (or more) different nitrogens with different protecting groups such that one such protecting group can be selectively removed while leaving the second protecting group in place. For example, the trityl and benzyl protecting groups can be used in this way, the trityl group being removable in the presence of the benzyl group under acidic conditions.

The requirements for protecting groups in Schemes I to IX are generally well recognized by one skilled in the art of organic chemical synthesis. It is recognized that conditions for introduction and removal of protecting groups should not undesirably alter any other groups in the molecule. In Schemes I to IX, m is 3 or 4; P is a suitable protecting group; r is 1 or 2; $R_{11}$ is R, $R_1$, or a suitable nitrogen protecting group; $R_{12}$ is $R_2$ or a suitable protecting group; $R_{13}$ is R, $R_1$, or a suitable nitrogen protecting group; $R_{14}$ is $R_2$ or a suitable nitrogen protecting group; with the proviso that when $R_{11}$ is $R_1$, then $R_{12}$ is $R_2$, $R_{13}$ is not $R_1$, and $R_{14}$ is not $R_2$; when $R_{13}$ is $R_1$, then $R_{14}$ is $R_2$, $R_{11}$ is not $R_1$, and $R_{12}$ is not $R_2$; when $R_{12}$ is $R_2$, then $R_{11}$ is $R_1$; when $R_{14}$ is $R_2$, then $R_{13}$ is $R_1$; when one of $R_{11}$ and $R_{13}$ is R the other of $R_{11}$ and $R_{13}$ is not R. In this way $R_{11}$, $R_{12}$, $R_{13}$, and $R_{14}$ are defined so that Scheme I shows that either the ultimate amide nitrogen atom or the ultimate $NR_1R_2$ nitrogen atom can be introduced first (Scheme I, step 10) followed by the introduction of the other (Scheme I, step 11).

Examples of suitable nitrogen protecting groups are:
(1) benzyl ($C_6H_5$—$CH_2$—);
(2) triphenylmethyl(trityl, ($C_6H_5)_3C$);
(3) para-toluenesulfonyl (p—$CH_3$—$C_6H_4$—$SO_2$—); and
(4) trialkylsilyl, for example, trimethylsilyl (($CH_3)_3Si$—) or tertiary butyldimethylsilyl (($CH_3)_3Si(CH_3)_2$—) and the like.
(5) tert-butoxycarbonyl (t-BOC),
(6) benzyloxycarbonyl,
(7) trifluoroalkanoyl, e.g., trifluoroacetyl, trifluoropropionyl,
(8) diphenyl(methyl)silyl,
(9) methanesulfonyl, and the like.

Introduction and removal of such nitrogen protecting groups are well known in the art or organic chemistry: See, for example, (1) J. F. W. McOmie, Advances in Organic Chemistry, Vol. 3, pages 191-281 (1963);

(2) R. A. Boissonas, Advances in Organic Chemistry, Vol. 3, pages 159-190 (1963);

(3) "Protective Groups in Organic Chemistry", J. F. W. McOmie, Ed., Plenum Press, New York, 1973, pg 74, and (4) *Protective Groups in Organic Synthesis*, Theodora W. Greene, John Wiley and Sons, New York, 1981.

Syntheses of the requisite material compounds are outlined in Schemes I to IX.

SCHEME I

In the Scheme I reaction, wherein Z is oxygen, the following comments are offered on the respective chemical step reactions.

1. The reaction between the bromoalkanol and the ethyl vinyl ether is conducted in the presence of dichloroacetic acid at about 23° to 50° C. to form the bromoalkyl ethoxyethyl ether shown at the beginning of step 2.

2. The bromoalkyl ethoxyethyl ether is reacted in step (a) with metallic lithium in diethyl ether or THF as solvent at about −20° to 0° C. Lithium containing about 0.6 to 1% sodium is preferred. In step (b) the monoethylene ketal of cyclohexane-1,4-dione is added dropwise in diethyl ether or THF to the organolithium solution formed in step (a) to form the β-ethoxyethoxyalkyl-1,4-dioxaspiro[4.5]decan-8-ol shown at the beginning of step 3.

3. A mild selective acidic hydrolysis of the acetal-ether is accomplished by treatment of the above cyclohexan-1-ol derivative with (a) an acidic ion exchange resin (Dowex-50 W-X8) in methanol at about 23° C. for one to 6 hours, (b) with an ethanol/water/hydrochloric acid (57.6/38.6/3.8 v/v) mixture at about 23° C. for 0.25 to 4 hours, to remove the ethyl acetal group and form the dihydroxy compound shown at the beginning of step 4.

4. The dihydroxy compound from step 3 is cyclized by treatment with methanesulfonyl chloride and two equivalents of triethylamine in methylene chloride at about 0° to 41° C.

5. The cyclized mono-oxy ketal is then subjected to acid hydrolysis (a) with 3 to 7% v/v aqueous perchloric acid ($HClO_4$) in THF at 40° to 80° C., or (b) with 1 to 4 N aqueous hydrochloric acid in acetone at about 23° to 60° C. to convert the ketal ring to the keto (—C(O)—) group compound shown at the beginning of step 6.

6. The ketone product from step 5 is treated (a) with lithium aluminum hydride in diethyl ether or THF at about 23° to reflux or (b) with sodium borohydride in methanol or ethanol at about 23° to 80° C., to form the spiro alkanol shown at the beginning of step 7.

7. The cyclohexanol derivative from step 6 is treated with p-toluenesulfonyl chloride in the presence of pyridine at about −20° C. to 0° C. for about 18 to 72 hours to form the p-toluenesulfonyl-(tosyl) structure shown at the beginning of step 8.

8. The tosyl group on the structure shown at the beginning of step 8 is eliminated by treatment with either (a) 1,8-diazabicyclo[5.4.0]undecene-5(DBU) at 80° to 120° C. or (b) with 1,5-diazabicyclo[4.3.0]nonene-5(DBN) at 80° to 120° C., to form the unsaturated ring compound (olefin) shown at the beginning of step 9.

9. The olefin from step 8 is epoxidized preferably by treatment with m-chloroperoxybenzoic acid in methylene dichloride at about −20° to 23° C. Other solvents such as hexane, carbon tetrachloride, benzene, chloroform, ethyl acetate and diethyl ether may be used in place of methylene chloride, or in admixture therewith, above their freezing points. Other peroxy acids, e.g., peroxyacetic, peroxybenzoic, p-nitroperoxybenzoic, monoperoxyphthalic, peroxylauric, peroxytrifluoroacetic and peroxyformic acids may be used in place of m-chloroperoxybenzoic acid in appropriate solvents therefor.

Alternatively, the olefin may be epoxidized with vanadyl acetyl acetonate [VO(AcAc)$_2$], tert-butyl hydroperoxide in benzene at about 23° C., or with molybdenum hexacarbonyl [Mo(CO)$_6$], tert-butylhydroperoxide in benzene at 23° C. to reflux to form the epoxide shown at the beginning of step 10.

10. The epoxide from step 9 is then opened with a secondary amine by any of various procedures to form the hydroxy-amine compound shown at the beginning of step 11.

(a) The epoxide can be treated with the secondary amine, e.g., with an HNR$_{11}$R$_{12}$ amine with no solvent at about 23° to 150° C., (b) The epoxide can be treated with the secondary amine, HNR$_{11}$R$_{12}$ in water at about 23° to 100° C., (c) The epoxide can be treated with the secondary amine, HNR$_{11}$R$_{12}$ in a mixture of N,N-dimethylformamide (DMF), dimethylsulfoxide (DMSO) and ethanol at from 23°-reflux temperature of the mixture, or (d) The epoxide can be opened with the secondary amine, HNR$_{11}$R$_{12}$ on an aluminum oxide carrier, to form the hydroxyamine structure shown at the beginning of step 11.

Depending upon the reaction conditions and the selected reagents, this epoxide opening reaction can give rise to up to 4 isomers which may, if convenient, be separated at this stage by chromatography or carried further in this reaction sequence as a mixture through the next step.

Depending on the structure of the final target molecule, it may be advantageous at this stage to utilize a secondary amine such as methyl(benzyl)amine, ethyl(benzyl)amine, propyl(benzyl)amine or dibenzylamine. The N-benzyl-protecting group would be removed at a later stage in the process. (See step 12 below)

11. (a) The hydroxy-amine from step 10 is treated with methanesulfonyl chloride and triethylamine in methylene chloride at about 0° C. to form the intermediate methanesulfonate (mesylate) bicyclic amine, (b) The crude amine-mesylate from step 11(a) is treated with ammonia, a primary amine (HNR$_{13}$R$_{14}$) or secondary amine (HNR$_{13}$R$_{14}$). The treatment can be conducted (11b1) using the selected nitrogen compound (ammonia, primary or secondary amine), no solvent at from about 23° C. to reflux temperature or in a sealed reaction bomb up to about 150° C., or (11b2) using the amine, as above, in water at about 23° C. to reflux temperature.

If isomerically pure amino-alcohols are used in Step 11 as starting materials, two regioisomeric diamine products are possible. If a mixture of amino-alcohols is used a total of four isomeric diamine products are possible. Chromatographic separation of the diamine isomers may be performed at this stage.

12. Amine protection and deprotection.

A suitable diamine precursor (II and IIa) for the final acylation must have only one of the two amino nitrogens from step 11 bearing a nitrogen-hydrogen bond. Depending upon the desired structure of the final target molecule (Ia) several situations may be considered at this point.

(a) One of the amino substituents R$_{11}$, R$_{12}$, R$_{13}$, R$_{14}$ (Step 12) is a benzyl group while the remaining three are non-removable R$_1$ and R$_2$ defined groups.

1. Catalytic hydrogenolysis of the diamine using 10% palladium on carbon as catalyst in ethanol or methanol as a solvent with or without an acidic catalyst, e.g., perchloric acid or hydrochloric acid.

2. Subjecting the benzyl-substituted diamine to dissolving metal reduction using lithium metal in liquid ammonia.

(b) The diamine nitrogen to be acylated can bear an N-alkyl and N-benzyl group or two N-benzyl groups and the other amino nitrogen bears one or two hydrogens;

1. The primary or secondary amine must first be protected before acylation. Suitable protecting groups are (a) tert-butoxycarbonyl (BOC), (b) benzyloxycarbonyl, or (c) trifluoroacetyl.

2. The N-benzyl group is cleaved as in step 12a, supra.

(c) The diamine (protected or non-protected as necessary) is acylated, as described above, and (d) The amino nitrogen protecting groups are removed, by known procedures, which do not undesirably alter the other parts of the molecule.

For preparing compounds according to Scheme II, wherein Z is NR$_3$—, and R$_3$ is shown as an N-benzoyl group, as an example, it should be noted that the starting cyclic cyclohexanol derivative where r is 1 is known. See R. A. Johnson, et a., J. Org. Chem. 35, 622 (1970). For compounds where r is 2, the starting materials would be prepared as outlined in Scheme III.

SCHEME II

1. In Scheme II, Step 1, the hydroxy group of the starting material is protected by (a) treatment with dihydropyran (P) in the presence of an acid, e.g., p-toluenesulfonic acid or hydrochloric acid, or by treatment with tert-butyl(dimethyl)silyl chloride or diphenyl(methyl)silyl chloride in the presence of imidazole and DMF, or the like.

2. Protected alcohol compound manipulation. Several possibilities exist:

A. If R$_3$ is not hydrogen:

1. The protected alcohol can be subjected to metal hydride reduction on the N-benzoyl group to convert it to the N-benzyl (a) by treatment with lithium aluminum hydride in diethyl ether or THF at about 0° to reflux, (b) by treatment with diborane (B$_2$H$_6$) in diethyl ether or THF at 0° to reflux, or (c) by treatment with sodium dihydrobis(methoxyethoxy)aluminate in diethyl ether or THF at about 0° to reflux.

2. The resultant N-benzyl group can be subjected to reductive cleavage to form the N—H ring protected alcohol by catalytic hydrogenolysis using 10% palladium on carbon as a catalyst in ethanol or methanol with or without an acid catalyst, e.g., acetic acid, perchloric acid, or the like, 3. If it is desired to form one or the other —NR$_3$— ring compounds, the N—H protected alcohol can be N-alkylated or N-acylated:

(a) by treatment with a methyl, ethyl or propyl chloride or bromide to form the respective N—C$_1$ to C$_3$-alkyl ring protected alcohol, in the presence of a base such as sodium hydride, potassium hydride or butyllithium in DMF, THF, or DMSO, (b) by reductive alkylation using formaldehyde, acetaldehyde or propionaldehyde in methanol in the presence of excess sodium cyanoborohydride, or (c) by an N-acylation procedure using procedures outlined hereinabove.

B. If $R_3$ is hydrogen:

1. Following reduction and cleavage steps 1 and 2 in Scheme II, Section 2A, hereinabove, 2. Protect the resultant secondary amine nitrogen using, for example, (a) methanesulfonyl chloride, or (b) benzyloxycarbonyl chloride.

3. Deprotect the ring hydroxyl group (remove the P group) with acid, e.g., with hydrochloric acid or p-toluenesulfonic acid, or with tetra(n-butyl)ammonium fluoride, and then 4. Proceed with the tosylation, elimination, epoxidation, epoxide opening, mesylate formation, diamine formation and amine protection and acylation steps as set forth in Scheme I, steps 7 to 12, hereinabove.

SCHEME III

Scheme III outlines a procedure for making a 1-azaspiro[5.5]undecan-9-ol.

1. The 1-azaspiro[5.5]undecane starting material can be prepared by the method described by H. Hodjat, et al., in J. Heterocyclic Chem., 9, 1081 (1972). This starting material is treated with benzoyl chloride in pyridine to form the N-benzoyl-1-azaspiro-[5.5]undecane, shown at the beginning of step 2.

2. The N-benzoyl compound from step 1 is subjected to hydroxylation by the microorganism, *Sporotrichium sulfurescens V. Begma* (ATCC 7159) by a microbiological oxidation procedure carried out as described by R. A. Johnson, et al., in J. Org. Chem., 35, 622 (1970).

SCHEME IV

The procedure of Scheme IV can be used to prepare compounds where Z is to be bivalent sulfur (—S—), sulfinyl (—S(O)—) or sulfonyl (—S(O)$_2$—).

1. The bromoalkylthiol starting material is protected (P) by either (a) treatment with dihydropyran and acid, e.g., p-toluenesulfonic acid or hydrochloric acid, or (b) ethyl vinyl ether and acid, e.g., dichloroacetic acid, to give the protected bromoalkylthiol at the beginning of step 2.

2. The protected bromoalkylthiol is then (a) metalated by either:

1. Treatment with lithium metal in diethyl ether or THF at about $-20°$ to $0°$ C. (Lithium wire containing 0.6% to 1% sodium is preferred), or 2. Treatment with metallic magnesium in diethyl ether or THF as solvent at about $-20°$ C. to reflux and then (b) the organometallic protected thiol is treated by the dropwise addition thereto of the monoethylene ketal of cyclohexane-1,4-dione in diethyl ether or THF at about $0°$ to reflux to form the ketal addition product shown at the beginning of step 3.

3. The ketal addition product from step 2 is treated, e.g., with acid to effect an acid catalyzed cleavage of the ketal or acetal and deprotection of the sulfur, accompanied by the dehydrative spirocyclization to form the thio-ring-cyclohexanone shown at the beginning of step 4, e.g., by:

(a) treatment with p-toluenesulfonic acid in a solvent such as THF, acetone, methanol, ethanol, or water at $0°$ to $100°$ C., or (b) by treatment with hydrochloric acid in THF, acetone, methanol or ethanol or water at about $0°$ to $100°$ C., or (c) by use of other mineral acids in place of those indicated above.

4. The ketone product from step 3 is reduced to the alcohol by either:

(a) treatment with lithium aluminum hydride in diethyl ether or THF at about $23°$ to reflux, or (b) treatment with sodium borohydride in methanol or ethanol at $23°$ to $80°$ C.

5. The alcohol from step 4 is tosylated by treatment with p-toluenesulfonyl chloride in pyridine at about $0°$ to $20°$ C.

6. The tosylated product from step 5 is treated to eliminate the tosyl group, e.g., (a) by treatment with 1,8-diazabicyclo[5.4.0]undecene-5(DBU) at about $80°$ to $120°$ C., or (b) by treatment with 1,5-diazabicyclo[4.3.0]nonene-5(DBN) at about $80°$ to $120°$ C. to form the cyclic olefin shown at the beginning of step 7.

7. In the cyclic olefin from step 6 the ring sulfur is oxidized to the corresponding sulfoxide or sulfone, if desired, and the double bond is epoxidized by:

(a) treatment of the cyclic olefin with m-chloroperoxybenzoic acid (or other peracid, as indicated above) in methylene chloride at about $-20°$ to $23°$ C. Other solvents such as hexane, carbon tetrachloride, benzene, chloroform, ethyl acetate, and diethyl ether may be used at temperatures above their freezing points. Other peroxy acids, e.g., peroxyacetic, peroxybenzoic, p-nitroperoxybenzoic, monoperoxyphthalic, peroxylauric, peroxytrifluoroacetic in appropriate solvents therefor can be used.

(b) treatment with aqueous sodium metaperiodate followed by meta-chloroperoxybenzoic acid treatment as in part (a) above.

8. The synthesis of the target compounds Ia where Z is —S—, —S(O)— or —S(O)$_2$— can be completed by following the expoxide opening, mesylation, diamine formation and amine protection and acylation procedures of steps 10 to 12 of Scheme I. The oxidation state of sulfur (thioether, sulfoxide, or sulfone) can be adjusted by known methods just prior to final acylation. See "Organic Chemistry of Sulfur" by S. Oae, Plenum Press, N.Y. and London (1977).

SCHEME V

1. Procedures according to Scheme V are preferred to prepare intermediates to compounds of this invention wherein Z is NR$_3$. In Scheme V, Step 1, the benzene ring of the starting amine is converted to the non-conjugated diene by reduction with sodium or lithium in refluxing liquid ammonia in the presence of ethanol and an ether cosolvent.

2. The diene-amine is converted to the sulfonamide by treatment with methanesulfonyl chloride in the presence of triethylamine at $0°$ to $23°$ C. in methylene chloride.

3. The sulfonamide is cyclized by treatment with an acid in a suitable solvent, e.g., (a) treatment with trifluoromethanesulfonic acid in benzene, diethyl ether, or methylene chloride at $0°$ to $23°$ C.

It may be advantageous to remove the methanesulfonyl group at this stage of the synthesis (see step 4 immediately below) or it may be beneficial to retain the methanesulfonyl group as a nitrogen protecting group and proceed with epoxidation, epoxide opening, mesylate formation, and diamine formation as in Scheme I, steps 9–11. At this point the methanesulfonyl group of the sulfonamido-diamine with any diamine N—H bonds suitably protected, is removed (see step 4 immediately below) and if necessary the resulting N—H bond is suitably protected, e.g., with a tert-butyloxycarbonyl group. The diamine nitrogen to be acylated is then deprotected, e.g., by hydrogenation over a palladium on carbon catalyst in ethanol if the benzyl protecting group was utilized, followed by acylation as described above. If $R_3$ is to be other than hydrogen, $R_3$ is introduced at this point by N-alkylation or N-acylation as described hereinabove for Scheme II. Finally any necessary nitrogen deprotection is effected to produce a 1-azaspiro-amino-amide of this invention.

4. Removal of the methanesulfonyl group in either case recited in step 3 immediately above is accomplished by reaction with sodium dihydrobis(2-methoxyethoxy)aluminate in benzene, toluene, or xylene solvent at 23° to reflux.

The process of Scheme VI is a preferred method for making certain 1-thiaspiro-olefin intermediates, and the steps are described as follows.

SCHEME VI

1. Reduction to the unconjugated diene using lithium or sodium metal in liquid ammonia in the presence of ethanol with or without an ether (diethyl ether or THF) cosolvent at −78° to reflux.

2. Spirocyclization by heating with an acid catalyst such as hydrochloric, p-toluenesulfonic or trifluoromethanesulfonic acid or the like, with or without a solvent such as DMF, THF, N,N-dimethylsulfoxide (DMSO), or benzene.

SCHEME VII

The process of Scheme VII is used to prepare 1-oxaspiro-olefin intermediates to make compounds of this invention wherein Z=O, p is zero, and n=3, and the steps are described as follows.

1a. The protected bromoalkanol is metalated
   (a) lithium wire at −20° to 23° C. in diethyl ether (Et$_2$O) or THF, or
   (b) with tertiary butyllithium at −78° in Et$_2$O or THF.

1b. To the lithium reagent prepared in step 1a is added 2-cyclohexene-1-ol in Et$_2$O or THF at −78° to reflux.

2. The acetal protecting group is removed by mild acid hydrolysis with:
   (a) an ion exchange resin (Dowex-50-WX8) in methanol at about 23° C., or
   (b) with ethanol/water/hydrochloric acid (57.6/38.6/3.8, v/v/v) at about 23° C.

3. Spirocyclization using an acid catalyst such as p-toluenesulfonic, hydrochloric or trifluoromethanesulfonic acid, etc., without solvent at 23° to 120° or with solvent such as DMF, THF, benzene or DMSO at 23° to reflux.

SCHEME VIII

The process of Scheme VIII is used to prepare 1-azaspiro-olefin intermediates to make compounds of this invention wherein Z=NR$_3$, p is zero, and n=3, and the steps are described as follows.

1a. The protected bromoalkanol is metalated
   (a) lithium wire at −20° to 23° C. in diethyl ether (Et$_2$O) or THF, or
   (b) with tertiary butyllithium at −78° in Et$_2$O or THF.

1b. To the lithium reagent prepared in step 1a is added 2-cyclohexene-1-ol in Et$_2$O or THF at −78° to reflux.

2. Acid catalyzed azaspirocyclization using acids such as p-toluenesulfonic, hydrobromic or trifluoromethanesulfonic acid, etc., with or without a solvent such as methanol, ethanol, THF or benzene.

3. Reductive cleavage of methanesulfonyl at the desired stage as in steps 3 and 4, Scheme V.

SCHEME IX

The process of Scheme IX is used to prepare 1-thiaspiro-olefin intermediates to make compounds of this invention wherein Z=S, SO, or SO$_2$, p is zero, and n=3, and the steps are described as follows.

1a. The protected bromoalkanol is metalated
   (a) lithium wire at −20° to 23° C. in diethyl ether (Et$_2$O) or THF, or
   (b) with tertiary butyllithium at −78° in Et$_2$O or THF.

1b. To the lithium reagent prepared in step 1a is added 2-cyclohexene-1-ol in Et$_2$O or THF at −78° to reflux.

2. The protecting group is cleaved by:
   (a) stirring in methanol solution in the presence of an acidic resin such as Dowex-50-WX8 resin or other acid catalyst such as hydrochloric, p-toluenesulfonic or hydrobromic in acetic acid, methanol or ethanol, or
   (b) treating with boron trifluoride etherate in acetic acid.

3. Spirothiacyclization using acids such as p-toluenesulfonic, hydrochloric, trifluoromethanesulfonic with or without solvents such as methanol, ethanol, THF or DMF.

The cyclized olefins produced by the processes of Charts V to IX are further reacted by epoxidation, epoxide opening, mesylate formation, diamine formation and amine protection and acylation steps as set forth in Scheme I, steps 9–12 and Scheme IV, steps 7 and 8, hereinabove.

The compounds having the nitrogen containing groups at positions 1 and 2 of structure (I) in a cis orientation are prepared by using (1) methodology herein described to construct the Z-containing ring, (2) methodology described in the Ser. No. 06/252,535 and Ser. No. 06/252,536 applications described hereinabove to construct the cis diamine orientation, and (3) methodology described herein for the acylation of the cis diamines. The cis-compounds are included within the general structure I, wherein the m, n, p, A, E, R, $R_1$, $R_2$, X, Y and Z are as defined hereinabove.

The compounds of formula I wherein E is to be bivalent sulfur are made by methodology disclosed in applications Ser. No. 06/252,535 and 06/256,536, referred to hereinabove.

The term "dosage unit form" as used in this specification and in the claims refers to physically discrete units suitable as unitary dosages for mammalian subjects, each unit containing as the essential active ingredient a predetermined quantity of a compound of this invention with the required pharmaceutical means which adapt said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification under preferred embodiments, those being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected form the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of these amino-amide active ingredients in combination with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must sterile and must be fluid to the extent that easy syringeabil·ity exists. Such preparations must be stable under the conditions of manufacture and storage, and ordinarily contain in addition to the principal solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars or sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservative, isotonic agents and the like constitute the pharmaceutical means which adapt the preparations for systemic administration.

The pharmaceutical dosage unit forms of the compounds of this invention are prepared in accordance with the preceding general description to provdie from about 0.5 to about 350 mg of the essential active ingredient per dosage unit form, which as aforesaid may be in the form of a semi-solid or solid, topical, oral or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain analgesic effects within the aforesaid effective non-toxic range. Expressed otherwise, when used systemically, an amount of the essential active ingredient is provided to a recipient within a range from about 0.01 mg/kg to about 5 mg/kg of body weight of the recipient.

Preferred dosages for most applications are 0.05 to 2.0 mg/kg of body weight. In a topical semi-solid ointment formulation the concentration of the active ingredient may be 0.2–10%, preferably 0.5–5% in a carrier, such as a pharmaceutical cream base.

The useful pharmaceutical dosage unit forms of these compounds in pharmaceutical formulations are preferably adapted for systemic administration to obtain analgesic effects comprising an effective, non-toxic amount of a compound according to Formula I or as its pharmacologically acceptable salt.

Further, the invention relates to methods of obtaining analgesic effects in mammals, for example, humans and valuable warm-blooded animals such as dogs, cats, horses and other commercially valuable animals, by administering systemically to the mammals the aforesaid pharmaceutical dosage unit forms supplying an effective, non-toxic amount for analgesic effets. These preferred compounds have an advantage, to a greater extent, depending upon the particular compound, of having lower physical dependence liability than known analgesic compounds such as morphine and methadone, as shown by evaluation of representative compounds and those standard analgesic drug compounds in various pharmacological test procedures which measure analgesia and the physical dependence liability of the test compounds in standard laboratory test animals.

Representative examples of these Formula I compounds have $ED_{50}$ values of less than about 75 mg/kg s.c. (subcutaneous administration) in standard laboratory animal analgesic tests such as the tail flick, pinch, and hydrochloric acid or air writhing tests, and the more potent of them have $ED_{50}$ values of less than 10 mg/kg (s.c.) in these tests, while at the same time giving quite high values (greater than 250 mg/kg s.c.) in the naloxone jumping test thus possessing low apparent physical dependence liability as compared to commercial analgesics used as standards. The procedures used to determine these properties of these new compounds were essentially those of Way et al., (Way, E. L. et al., "Simultaneous Quantitative Assessment of Morphine Tolerance and Physical Dependence", *J. Pharmacol. Exp. Ther.*, 167, pp. 1–8 (1969)) and Saelens et al., (Saelens, J. K. et al., "The Mouse Jumping Test—A Simple Screening Method to Estimate the Physical Dependence Capacity of Analgesics", *Arch. Int. Pharmacodyn.*, 190, pp. 213–218 (1971)). Statistical effective doses ($ED_{50}$ values) and 95% confidence limits were calculated by the method of Spearman and Karber (Finney, D. J., "Statistical Methods in Biological Assay", Hafner Publ. (1952)).

For example, representative preferred compounds of Formula I give low analgesic $ED_{50}$ values (less than about 10 mg of test compound/kg of animal body weight, subcutaneous administration route) in standard laboratory animal tests while at the same time possessing quite high $ED_{50}$ values (greater than 250 mg/kg s.c.) in the naxolone jumping test, evidencing substantial freedom from apparent physical dependence liability. In contrast, known analgesic drugs such as morphine and methadone exhibit analgesic $ED_{50}$ values of les than 2 mg/kg s.c., respectively, in these standard analgesic tail flick, pinch and writhing tests, but are known to have high apparent physical dependence liability effects, and this is confirmed by their (morphine and methadone) having relatively low naloxone jumping $ED_{50}$ values ranging form 12 to 30 mg/kg s.c. Other representative compounds of this invention have analgesic potencies somewhat less than the preferred compounds (analgesic activity $ED_{50}$ values up to about 75 mg/kg s.c., in these standard tests), and some such compounds still are characterized by having only low to moderate apparent physical dependence liability.

This invention is further exemplified by the following detailed examples, the procedures of which can be used to prepare compounds of this invention, but these examples are not intended to limit the scope of the invention. All temperatures are in degrees centigrade unless otherwise noted. For brevity, Hg means mercury, bp means boiling point, $CH_2Cl_2$ means methylene chloride solvent, $K_2CO_3$, $MgSO_4$ or $Na_2SO_4$ means the organic layer was dried over anhydrous forms of these salts, mp means melting point, NMR means a nuclear magnetic resonance spectrum, and DBN means 1,5-diazobicyclo[4.3.0]non-5-ene; h means hour(s), $N_2$ means nitrogen, tlc means thin layer chromatography procedures, $Na_2SO_3$ means sodium sulfite, $NaHCO_3$ means sodium bicarbonate, DMSO is dimethylsulfoxide, Skellysolve B (or Skelly B) is a tradename for a solvent of essentially n-hexane, bp 60°–68° C. (Merck Index, Ninth Edition (1976) page 1106), $Et_2O$ means diethyl ether, MeOH means methanol, THF means tetrahydrofuran, $H_2O$ means water, $CHCl_3$ means chloroform, brine is saturated aqueous sodium chloride solution, DMF means N,N-dimethylformamide, $Et_3N$ is triethylamine, HRMS means high resolution mass spectrum, EtOAc means ethyl acetate, GC for (g.c.) means gas chromatography, GLPC means gas liquid phase chromatography.

EXAMPLE 1

(±)-(5α,7α,8β)-3,4-dichloro-N-methyl-N-[7-(1-pyrrolidinyl)-1-oxaspiro[4.5]dec-8-yl]benzeneacetamide Step A.
8-[3-(1-ethoxyethoxy)propyl]-1,4-dioxaspiro[4.5]decan-8-ol To an oven-dried two liter three-necked round bottom flask equipped with an addition funnel, low temperature thermometer, magnetic stir bar, positive nitrogen pressure inlet and a serum cup, there was placed 12.03 g (1.79 g atoms) of lithium [⅛ inch lithium wire containing 0.6% sodium—Lithium Corporation of America—cut into approximately 1 inch pieces under a flow of nitrogen] in one liter of dry diethyl ether. (Fresh cans of anhydrous ethyl ether were used without further drying). Then 161 g (0.76 mol) of ethyl 3-bromopropyl acetaldehyde acetal (J. Org. Chem, 37, 1947 (1972), P. E. Eaton, et al.) was added as follows. An approximately 25 ml portion of the bromide (neat) was added and the temperature of the reaction mixture was monitored. When the temperature reached 28° C. the reaction flask was immersed in a dry ice/carbon tetrachloride cooling bath (about −20° C.) and the rate of addition of the remaining bromide reactant was controlled to maintain a reaction temperature of about −5° to 0° C. After the addition of the bromide was completed the reaction mixture was stirred at about −20° C. for one hour and then transferred via a canula (syringe and needle) to an oven dried three-necked three liter round bottom flask equipped with an addition funnel, a magnetic stir bar, a positive nitrogen inlet and cooled externally by an ice-water bath, to obtain and maintain the ethoxyethoxypropyl lithium intermediate.

To the above lithiated intermediate there was added dropwise a solution of 85.8 g (0.55 mol) of 8-oxo-1,4-dioxaspiro[4.5]decane in one liter of dry diethyl ether (fresh cans, as above) over a period of about 2.5 hr. The resulting reaction mixture was allowed to warm slowly to room temperature and then poured into two liters of ice cold half saturated ammonium chloride in water solution. The phases were separated and the aqueous phase was extracted with one liter of diethyl ether. The ether layers were combined and washed with brine solution, dried over sodium sulfate, and then the ether solvent was removed under reduced pressure to leave, after drying to 45° C. (0.25 mm.Hg) for 14 hours, 142.15 g of a light yellow oil, the above named decan-8-ol acetal intermediate, which was of sufficient purity to use in the next step. A small sample of the named oil was distilled at reduced pressure to obtain a purer material bp 135°–140° C. (0.01 mmHg). The nuclear magnetic resonance spectrum (using $CDCl_3$ solvent), was consistent with the above named decan-8-ol acetal compound.

Step B. 1,4,9-Trioxadispiro[4.2.4.2]tetradecane

To a solution of 142 g (0.52 mol) of the crude decan-8-ol acetal from Step A in one liter of methanol there was added 50 g of an acid resin (Dowex ® 50W-X8 (200–400 mesh) and the mixture was stirred at room temperature for 2.5 hr. The reaction mixture was filtered through a filter aid pad (Celite) and the filtrate was evaporated to leave, after drying at 55° C. (0.25 mmHg) for 16 hr, 108.1 g (96% yield) of a crude diol intermediate which was of sufficient purity for the next transformation. The NMR was consistent with the expected intermediate product.

To a solution of 108 g (0.5 mol) of the above crude diol mixed with 116.3 g (1.15 mol) of triethylamine in 2 liters of methylene chloride, cooled to 0° C. in an ice bath there was added dropwise over 2 hr a solution of 65.8 g (0.575 mol) of methanesulfonyl chloride in 500 ml of methylene chloride. After the addition was completed the reaction mixture was stirred for 16 hr (ice not replenished) and then washed once with water, dried over magnesium sulfate and the solvent was removed in vacuo.

The crude product residue was distilled at reduced pressure to give 77.6 g (78% yield) of a water white liquid which crystallized upon standing at room temperature, bp 84°–87° C. (0.7 mmHg), mp 48°–50° C. The NMR was consistent with the above named tetradecane ketal compound.

Step C. 1-Oxaspiro[4.5]decan-8-one

To a solution of 75.5 g (0.38 mol) of the ketal tetradecane from Step B above in 400 ml of tetrahydrofuran (THF) there was added 300 ml of 5% aqueous perchloric acid and the mixture was heated to 70° C. for 18 hr. The resulting reaction mixture was cooled to room temperature and this distributed between 1.5 liters of saturated aqueous sodium bicarbonate solution and one liter of diethyl ether. The liquid phases were separated and the aqueous phase was extracted once with ethyl ether. The ether phases were combined, washed with brine solution, dried over magnesium sulfate and the solvent was removed in vacuo to leave as residue 53.9 g (92% yield) of a colorless liquid, with gas chromatography (GC) showed to contain 9% of the starting ketal. The NMR was consistent with the named decan-8-one compound, but showed the ketal impurity shoulder at 3.93 ppm. This named crude ketone/ketal was used for further transformation without additional purification.

An aliquot of this crude ketone/ketal was distilled at reduced pressure, bp 77°–84° C./0.8 mmHg.

Step D. 1-Oxaspiro[4.5]decan-8-ol, 4-methylbenzenesulfonate

To a suspension of 4.7 g (0.116 mol) of lithium aluminum hydride in 600 ml of dry diethyl ether there was added dropwise at a rate to maintain gentle reflux a solution of 53.9 g (0.35 mol) of 1-oxaspiro[4.5]decan-8-one, from Step C above, in 225 ml of dry ethyl ether. After the addition was completed the resulting reaction mixture was stirred at room temperature for 0.5 hr and quenched by dropwise addition of 10 ml of ethyl acetate, followed in succession by 4.7 ml of water, 4.7 ml of 15% aqueous sodium hydroxide and 14.1 ml of water. The resultant mixture was filtered, the filter cake was washed with diethyl ether and the solvent was removed in vacuo leaving 52.3 g of a light yellow liquid (of reduced ketone; crude alcohol) which was used without further purification. The NMR was consistent with the reduced ketone structure.

To a solution of 51.3 g (0.32 mol) of the crude alcohol reduction product from above in 700 ml of dry pyridine cooled to $-17°$ C. there was added a solution of 69 g (0.36 mol) of p-toluenesulfonyl chloride in 400 ml of dry pyridine (solution cooled to $0°$ C.), and the resultant mixture was stored at $-17°$ C. for 110 hr. The bulk of the pyridine was removed in vacuo and the residue was distributed between ethyl ether and water. The aqueous phase was extracted twice with ethyl ether, the combined ethyl ether liquid phases were extracted twice with ice cold 5% aqueous hydrochloric acid, once with saturated aqueous sodium bicarbonate, dried over magnesium sulfate and the solvent was removed in vacuo leaving 79 g (80% yield) of the titled 4-methylbenzenesulfonate as a white solid.

A small sample of the above sulfonate solid was recrystallized twice from diethyl ether; mp $82°-84°$ C. The NMR of the solid was consistent with the title named 4-methylbenzenesulfonate compound.

Anal. Calcd. for $C_{16}H_{22}O_4S$: C, 61.91; H, 7.14; S, 10.33. Found %: C, 61.64; H, 7.35; S, 10.24.

Step E. 1-Oxaspiro[4.5]dec-7-ene

A mixture of 79.0 g (0.27 mol) of 1-oxaspiro[4.5]decan-8-ol, 4-methyl benzenesulfonate (tosylate) from Step D above, and 50 g (0.33 mol) of 1,8-diazabicyclo[5.4.0]undecene-5(DBU) was heated at $100°$ C. for 8 hr. The resulting reaction mixture was cooled to room temperature and distributed between 600 ml of water and 200 ml of diethyl ether. The liquid phases were separated, the aqueous phase was extracted twice with 200 ml portions of ethyl ether, the ethereal phases were combined, washed twice with 10% aqueous hydrochloric acid, once with saturated aqueous sodium bicarbonate, once with brine solution, dried over sodium sulfate and the solvent was removed on a steam bath at atmospheric pressure through a 12 in. Vigreux column.

The crude product thus obtained was distilled at reduced pressure to give 23.8 g (64% yield) of the subtitled dec-7-ene compound: bp $62°-63°$ C. (3.25 mmHg). The NMR was consistent with the sub-titled compound.

Anal. Calcd for $C_9H_{14}O$: C, 78.21; H, 10.21. Found, %: C, 77.80; H, 10.21.

Step F.
($\pm$)-($1'\alpha,3'\beta,6'\alpha$)-dihydrospiro[furan-2(3H),3'-[7]-oxabicyclo-[4.1.0]heptane-(Isomer B, cis), and
($\pm$)-($1'\alpha,3'\alpha,6'\alpha$)-dihydrospiro[furan-2(3H),3'-[7]oxabicyclo[4.1.0]heptane-(Isomer A, trans)

To a solution of 20.0 g (0.145 mol) of 1-oxaspiro[4.5]dec-7-ene in 200 ml of dichloromethane there was added dropwise over a period of about 2.5 hr a solution of 32.3 g (about 0.16 mol) of m-chloro-peroxybenzoic acid (80–90%, Aldrich) in 600 ml of dichloromethane. The resulting reaction mixture was stirred at ambient temperature for one hr and then 100 ml of 10% aqueous sodium bisulfate was added. After stirring the resulting reaction mixture for one hr the mixture gave a negative starch iodine test. The reaction mixture was washed twice with one liter portions of half saturated aqueous sodium bicarbonate solution, dried over sodium sulfate and sodium carbonate and the solvent was then removed in vacuo at ambient temperature leaving 21.0 g of a light yellow liquid. Analysis of this liquid mixture by gas liquid phase chromatography (GLPC) showed it to be a 45:55 w/w mixture of Isomer A and Isomer B named above. The GLPC analysis was done using a 3% SE-30 column. Isomer A was assigned the trans epoxide and Isomer B was assigned the cis epoxide configuration on the basis of chemical conversion to a product of known stereochemistry.

A 1.0 g aliquot of the liquid mixture was removed and the remainder used in further chemical reactions without further purification.

The 1.0 g aliquot from above was chromatographed on 170 g of 40–63 micron (u) silica gel (Merck) eluting with 20% ethyl acetate/-benzene benzene mixture to give 170 mg of pure Isomer A above and 220 mg of pure Isomer B along with still mixed fractions.

For Isomer A: The NMR was consistent for the named Isomer A.
Anal. Calcd. for $C_9H_{14}O_2$: Mo. Wt. 154.0994. Found: 154.0985.

For Isomer B: The NMR was consistent for the named Isomer B.
Anal. Calcd. for $C_9H_4O_2$: Mol. Wt. 154.0994. Found: 154.0988.

Step G.
($\pm$)-($5\alpha,7\alpha,8\beta$)-1-[8-[methyl(phenylmethyl)amino]-1-oxa-spiro[4.5]dec-7-yl]pyrrolidine (Isomer A)
($\pm$)-($5\alpha,7\alpha,8\beta$)-1-[7-[methyl(phenylmethyl)amino]-1-oxa-spiro-[4.5]dec-8-yl]pyrrolidine (Isomer C).

A solution consisting of 10.0 g (about 65 mmol) of a mixture of the cis- and trans-1-oxaspiro[4.5]decan-7-ene oxides, from Step F above, 17.42 (0.14 mol) of benzyl(methyl)amine and 6 ml of water was heated at $90°$ C. for 18 hr. The resulting reaction mixture was allowed to cool to room temperature and distributed between 10% aqueous sodium hydroxide solution and dichloromethane. The phases were separated, the aqueous layer was extracted once with dichloromethane, the organic liquid layers were combined, dried over magnesium sulfate and the solvent was removed in vacuo. The crude product liquid residue thus obtained was distilled at reduced pressure to give 9.5 g of a mixture of aminoalcohols as a water white viscous oil, bp $150°-160°$ C. (0.005 mmHg).

To a solution of 9.0 g (34 mmol) of the amino-alcohol mixture, from above, and 4.1 g (37.3 mmol) of triethylamine in 125 ml of dichloromethane cooled to $0°$ C.

there was added dropwise a solution of 4.3 g (37.3 mmol) of methanesulfonyl chloride in 50 ml of dichloromethane. After the addition was completed the resulting mixture was stirred at 0° C. for one hr and then transferred to a separatory funnel. The resulting mixture was washed once with water, dried over magnesium sulfate and the solvent was removed in vacuo at ambient temperature leaving 13.8 g of crude methanesulfone (mesylate) intermediate.

The crude mesylate intermediate, from above, was treated with 31.5 g (0.44 mol) of pyrrolidine and 13 ml of water and the resulting mixture was heated under a reflux condenser at 65° C. for 16 hr. The bulk of the excess pyrrolidine was removed from the resulting reaction mixture on a rotary evaporator and the residue was distributed between 10% aqueous sodium hydroxide and dichloromethane. The aqueous layer was extracted once with dichloromethane, the organic layers were combined, dried over magnesium sulfate and the solvent was removed in vacuo leaving 9.8 g of a yellow oil. A thin layer chromatography (tlc) analysis of the crude product suggested a mixture of at least three diamine isomers.

The crude product was chromatographed on 1 kg. of 40-63 micron size silica gel (Merck) eluting with an ammonia/methanol/ethanol (0.8/7.2/92 v/v) mixture. Fractions containing pure isomers were combined to give 2.1 g of Isomer A, 2.5 g of isomer C, and 1.5 g of a mixture of isomer A, B, and C.

Isomer A: The NMR was consistent with the named Isomer A.

Mass Spectral Analysis: (m/e) 328 (M+), 244 (M+$CH_2$=$CCH_2CH_2CH_2O$)

166 ($CH_2(CH_2)_3N$=$CHCH$=$C(CH_2)_3O$)
160 ($CH_2$=$CHCH$=$N(CH_3)CH_2C_6H_5$)

Isomer C: The NMR was consistent with the named Isomer C.

Mass spectral analyses: (m/e) 328 (M+),
216 ($C_6H_5CH_2N(CH_3)$=$CHCH$=$C(CH_2)_3O$ and 10 ($CH_2$=$CHCH$=$N(CH_2)_3CH_2$).

Step H.

(±)-(5α,7α,8β)-3,4-dichloro-N-methyl-N-[7-(1-pyrrolidinyl)-1-oxaspiro[4.5]dec-8-yl]benzeneacetamide.

To a solution of 2.0 g (6.1 mmol) of Isomer A from Step G above in 100 ml of absolute ethanol there was added 2.0 g of 10% palladium on carbon and the mixture was shaken on a Parr apparatus under 35 psig of hydrogen pressure, to remove the N-benzyl protecting group. Once the uptake of hydrogen had ceased the reaction mixture was filtered through a filter aid pad (Celite), the pad was washed with several portions of ethanol and the filtrate was evaporated in vacuo leaving, after high vacuum drying, 1.3 g of the de-benzylated amine intermediate product (±)-(5α,7α,8β)-N-methyl-7-(1-pyrrolidinyl)-1-oxaspiro[4.5]decan-8-amine, as a colorless oil.

To a solution of 0.75 g (362 mmol) of 3,4-dichlorophenylacetic acid in 25 ml of dry tetrahydrofuran there was added (in a single batch) 0.59 g (3.62 mmol) of 1,1-carbonyldiimidazole and the resultant mixture was stirred at ambient temperature for one hour. A solution of 0.75 g (3.15 mmol) of the de-benzylated diamine, obtained hereinabove, in 20 ml of dry THF was added dropwise and the resultant mixture was stirred at ambient temperature for 18 hours. The bulk of the THF was removed on a rotary evaporator and the residue was distributed between ethyl ether and water. The liquid phases were separated and the ethereal liquid phase was washed once with water, once with brine solution, dried over magnesium sulfate and the solvent was removed in vacuo leaving 1.25 g of a white, waxy solid.

This crude amino-amide solid was crystallized twice from acetonitrile to give 0.8 g (54% yield) of the titled compound, mp 105.5°-106.5° C. The NMR and infrared spectrum (IR) were consistent with the named compound. It analyzed as follows:

Anal. Calcd. for $C_{22}H_{30}Cl_2N_2O_2$: C, 62.11; H, 7.11; Cl, 16.67; N, 6.59%. Found: C, 62.06, H, 7.19; Cl, 16.58; N, 6.39%.

An X-ray crystal structure determination on the titled compound confirms the regio- and stereochemical assignment.

The monohydrobromide of the titled compound was prepared by adding diethyl ether-hydrobromic acid to the free base in diethyl ether. The resultant precipitate was collected and recrystallized from a methanol/diethyl ether mixture to give white microcrystals, mp 209-210/C., of the monohydrobromide of the titled compound.

Anal. Calcd. for $C_{22}H_{31}N_2O_2Cl_2Br$: C, 52.18; H, 6.17; N, 5.53; Cl, 14.00; Br, 15.78. Found: C, 51.91; H, 6.20; N, 5.51; Cl, 13.92; Br, 15.69.

A preferred process for preparing the titled compound of Example 1, Part H, is the following. The epoxidation of 1-oxaspiro[4.5]dec-7-ene is carried out using m-chloroperoxybenzoic acid in diethyl ether solvent to give a mixture of epoxides enriched in the (1'α,3'β,6'α) isomer. This mixture of epoxides is reacted with pyrrolidine according to step 10 of Scheme I to produce a pyrrolidinyl-alcohol. This intermediate, according to step 11 of Scheme I, is converted to the mesylate, which is then reacted with benzyl(methyl)amine. The resulting diamine mixture is debenzylated according to step 12a or 12b of Scheme I and acylated as described hereinabove, and the product titled in Example 1, Part H, is purified by recrystallization from acetonitrile.

EXAMPLE 2

(±)-(5α,7α,8β)-4-bromo-N-methyl-N-[7-(1-pyrrolidinyl)-1-oxaspiro[4.5]dec-8-yl]benzamide To a solution of 0.54 g (2.28 mmol) of the de-benzylated diamine, from Step H of Example 1, and 0.28 g of triethylamine in 35 ml of dry diethyl ether there was added dropwise a solution of 0.55 g (2.5 mmol) of 4-bromobenzoyl chloride in 25 ml of dry diethyl ether. After the addition was complete the resulting reaction mixture was stirred at ambient temperature for 3 hr and then distributed between water and ethyl acetate. The phases were separated and the organic liquid phase was washed once with water, once with brine solution, dried over magnesium sulfate and the solvent removed in vacuo leaving 1.0 g of a white powder which was recrystallized twice from acetonitrile to give 0.7 g (74% yield) of the titled amino-amide as white crystals: mp 181°-185° C. (dec). The NMR, IR and mass spectral analyses were consistent with the named product. The elemental analysis was as follows:

Anal. Calcd. for $C_{21}H_{29}BrN_2O_2$: C, 59.85; H, 6.94; N, 6.65; Br, 18.96%. Found: C, 59.77; H, 7.00; N, 6.69; Br, 19.10%.

EXAMPLE 3

(±)-(5α,7α,8β)-3,4-dichloro-N-methyl-N-[8-(1-pyr-rolidinyl)-1-oxaspiro[4.5]dec-7-yl]benzeneacetamide, and its monohydrochloride-methanol solvate To a solution of 2.4 g (7.31 mmol) of the diamine, Isomer C, Step G of Example 1, in 100 ml of absolute ethanol there was added 2.4 g of 10% palladium on carbon and the resulting mixture was shaken on a Parr apparatus under 35 psig of hydrogen to de-benzylate the amine. After the uptake of hydrogen had ceased the resulting reaction mixture was filtered, the filter cake was washed thoroughly with absolute ethanol and the filtrate was evaporated in vacuo leaving 1.6 g of the debenzylated Isomer A amine as a colorless oil.

To a solution of 0.8 g (3.86 mmol) of 3,4-dichlorophenylacetic acid in dry THF there was added 0.63 g (3.86 mmol) of 1',1'-carbonyldiimidazole and the resulting mixture was stirred at ambient temperature for one hr. A solution of 0.8 g (3.36 mmol) of the de-benzylated Isomer A diamine, from above, in 20 ml of dry THF was added dropwise and the resultant solution was stirred at ambient temperature for 18 hr, to ensure complete reaction. The bulk of the THF was removed on a rotary evaporator and the residue was distributed between ethyl ether and water. The liquid phases were separated and the ethereal phase was concentrated in vacuo leaving 1.3 g of crude, titled product as an oil.

An ethereal solution of the crude product thus obtained was treated with ethereal hydrochloric acid and the resultant hydrochloride salt of the titled amino-amide precipitate was collected and recrystallized twice from a methanol/ethyl acetate (50/50 v/v) mixture to give 0.6 g of the titled amino-amide hydrochloride salt-solvate, mp 203°–210° C. The elemental analysis was as follows:

Anal. Calcd. for $C_{22}H_{30}Cl_2N_2O_2 \cdot HCl \cdot 0.5CH_3OH$; Calcd: C, 56.61; H, 6.86; N, 5.87; Cl, 22.28%. Found: C, 56.42; H, 6.91; N, 5.96; Cl, 22.99%.

EXAMPLE 4

(±)-(5ξ,6α,7β)-3,4-dichloro-N-methyl-N-[7-(1-pyrrolidinyl)-1-oxaspiro[4.5]dec-6-yl)benzeneacetamide

A. Preparation of 1-[3-(1-ethoxyethoxy)propyl]cyclohex-2-en-1-ol

In an oven dried 250 ml, 3 neck, round bottom flask fitted with magnetic stir bar, low temperature thermometer, septum and pressure equalizing addition funnel connected to a source of nitrogen there was placed 2.0 g (0.3 mol) of ⅛ in diameter lithium wire (containing 0.6% sodium) cut into ½ in pieces under a stream of nitrogen, and 125 ml of anhydrous diethyl ether. About 3 ml of ethyl 3-bromopropylacetaldehyde acetal was added dropwise with stirring under nitrogen. When the reaction temperature of the mixture had risen to 30° C. and the lithium wire began to turn shiny the reaction mixture was cooled to −5° C. in a dry ice/carbon tetrachloride mixture bath. The temperature of the mixture was maintained between 5° C. and 0° C. by the dropwise addition of the remainder of the 30.2 g (0.14 mol) of ethyl 3-bromopropylacetaldehyde acetal. After complete addition, the resultant mixture was stirred at dry ice/carbon tetrachloride cooling temperature (about −78° C.) for two hr, at which time the surface of the residual lithium wire had tarnished.

The organo-lithium intermediate compound formed in this above reaction mixture was transferred via a cannulus apparatus to a 250 ml oven dried, round bottom flask fitted with magnetic stir bar, septum, pressure equalizing additional funnel connected to a source of nitrogen and cooled to 0° C. in an ice/water bath. The addition funnel had been charged with 9.95 g (0.10 mol) of 2-cyclohexen-1-one and 100 ml of anhydrous ethyl ether. The cyclohexenone solution was added dropwise to the cold, stirred organolithium intermediate compound under nitrogen over a 1.5 hr period. The resultant mixture was stirred at 0° C. for one hr and then allowed to slowly warm to room temperature by stirring for 18 hr without replenishing the ice in the bath. The reaction mixture was poured into 250 ml of ice cold, ½ saturated ammonium chloride aqueous solution. The liquid phases were separated and the aqueous phase was extracted twice with 200 ml portions of diethyl ether. The combined ethereal liquid phases were washed with brine solution, dried over sodium sulfate and concentrated in vacuo to leave 21.4 g (93% yield) of the above named -cyclohex-2-ene-1-ol intermediate as a colorless oil which was used as such in the next step. The NMR of this intermediate was consistent with the above named intermediate compound.

B. Preparation of 1-Oxaspiro[4.5]dec-6-ene

A mixture of 21 g (0.10 mol) of the acetal, prepared as in part A hereinabove, 10 g of a cation exchange resin (Dowex® 50W-X8) (200 to 400 mesh) and 200 ml of methanol was stirred at room temperature for four hr to ensure complete reaction, and then filtered through a filter pad (Celite®). The filter pad was washed twice with 50 ml portions of methanol. The solvent from the combined filtrate and washings was removed from the mixture in vacuo to leave as residue 7.2 g (60% yield) of the sub-titled-dec-6-ene after distillation (bp 90°–96° C. at 25 mmHg). The NMR was consistent with the sub-titled-dec-6-ene. The mass spectrum analysis showed an m/e of 138(M+).

C. Preparation of (±)-(1'α,2'β,6'α)-Dihydrospiro[furan-2(3H),2'-[7]oxabicyclo[4.1.0]heptane] and (±)-(1'α,2'α,6'α)-dihydrospiro[furan-2(5H),2'-[7]-oxabicyclo[4.1.0]heptane (Isomer A is faster moving and Isomer B is slower moxing as described below)

To a stirred portion of 36 g (0.094 mol) of 1-oxaspiro[4.5]dec-6-ene, prepared as described hereinabove, 150 ml of ethylene chloride there was added dropwise 23 g of 80–90% m-chloroperbenzoic acid in 500 ml of methylene chloride over a 2 hr period. The reaction mixture was stirred for 18 hr at room temperature. To the resulting solution there was added 180 ml of 10% (W/V) aqueous sodium bisulfite solution and the resulting two liquid phase system was stirred rapidly for one hr (until a negative starch/iodide test result was obtained). Then, about 5 g of sodium bicarbonate was slowly added to the mixture in several batches with stirring. The resulting mixture was washed twice with ½ saturated sodium bicarbonate solution, once with saturated sodium chloride solution and dried over sodium sulfate/potassium carbonate. The solvent was removed and the residue was chromatographed on silica gel eluting with a 1:1 v/v hexane:ethyl acetate mixture to yield 9.5 g of the faster moving epoxide, Isomer A above, and 4.64 g of the slower moving epoxide, Isomer B above. The NMR spectra of each isomer A and B were consistent with the respective above named intermediate compounds, but the relative stereochemistry was undetermined. The mass spectrum of each isomer A and B showed an m/e=154(M+).

D. Preparation of (±)-[5ξ,6α,7β)-1-[6-[methyl(phenylmetyl)-amino]-1-oxaspiro[4.5]dec-7-yl]pyrrolidine A mixture of 3.65 g (0.024 mol) of 5,6-epoxy-1-oxaspiro[4.5]-decane, (Isomer A, hereinabove), 4.37 g (0.036 mol) of benzyl(methyl)amine and 2 ml of water was heated at 90° C. for 18 hr until the reaction was complete by thin layer chromatography (tlc) analysis. The reaction mixture was cooled in an ice bath to 0° C. and then 4 ml of 25% sodium hydroxide solution was added with stirring. The resulting basic mixture was extracted twice with 100 ml of methylene chloride. The combined organic liquid phase was dried over magnesium sulfate and removal of the solvent in vacuo left 4.9 g of an intermediate amino alcohol (See Scheme I, step 10) (±)-(5ε,6α,7β)-7-[methyl(phenyl-methyl)amino]-1-oxaspiro[4.5]decan-6-ol. The NMR and mass spectral analyses were consistent.

The above amino-alcohol intermediate thus formed, 1.98 g (0.018 mol) of triethylamine and 60 ml of methylene chloride were placed in an oven dried 250 ml round bottom flask equipped with a magnetic stir bar and pressure equalizing addition funnel connected to a source of nitrogen. The addition funnel was charged with 2.02 g (0.018 mol) of methylene chloride. The system was purged with nitrogen and cooled to 0° C. in an ice bath. The methanesulfonyl chloride (mesyl chloride) solution was added dropwise over a one hr period to the stirred amino alcohol reactant mixture. The resulting mixture was stirred for an additional one hr at 0° C. after complete addition to ensure complete reaction. The reaction mixture was washed once with 100 ml of water. The organic liquid phase was separated, dried over magnesium sulfate and the solvent was removed in vacuo to leave a residue 5.6 g of the crude mesylate intermediate.

To the above crude mesylate thus formed there was added 20 ml of pyrrolidine and 6 ml of water. The mixture was heated with stirring at 90° C. for 18 hr to ensure complete reaction. The excess pyrrolidine was removed in vacuo and the resulting crude residue was distributed between 100 ml of methylene chloride and 100 ml of 10% sodium hydroxide aqueous solution. The aqueous phase was extracted once with 50 ml of methylene chloride. The combined organic liquid phases were dried over magnesium sulfate and the solvent was removed in vacuo to leave 5.6 g (95% yield) of the above sub-titled pyrrolidine diamine derivative, after pumping at high vacuum (e.g., 0.1 mmHg) for 20 hr. The diamine derivative was used as such in the next step. The NMR and mass spectral analyses were consistent with the sub-titled diamine derivatives.

E. Preparation of (±)-(5ξ,6α,7β)-1-[6-methylamino-1-oxaspiro[4.5]dec-7-yl]pyrrolidine A mixture of 5.3 g (0.016 mol) of 6-benzyl(methyl)amino-7-pyrrolidinyl-1-oxaspiro[4.5]decane, from step D hereinabove, 5 g of 10% palladium on carbon and 150 ml of absolute ethanol was hydrogenated at about 40 psig for 4 days on a Parr apparatus to ensure complete reaction.

The hydrogenated mixture was filtered through a filter pad (Celite®)and the filter cake was washed twice with 50 ml portions of absolute ethanol. Removal of the solvent in vacuo left 3.11 g (82% yield) of the sub-titled pyrrolidinyl diamine intermediate as a colorless oil which was used as such in the next step. The NMR and mass spectral analyses of samples of this diamine oil were consistent with the sub-titled compounds.

F. (±)-(5ξ,6α,7β)-3,4-Dichloro-N-methyl-N-[7-(1-pyrrolidinyl)-1-oxaspiro[4.5]dec-6-yl]benzeneacetamide In a 50 ml oven dried round bottom flask fitted with a magnetic stir bar and a pressure equalizing addition funnel connected to a source of nitrogen there was placed 1.44 g (7.0 mmol) of 3,4-dichlorophenylacetic acid and 15 ml of THF (dried over 3A molecular sieves). To the stirred mixture there was added in three batches, as a solid, 1.13 g (7.0 mmol) of 1,1-carbonyldiimidazole over a 15 min period. The apparatus was flushed with nitrogen and the resultant mixture was stirred at room temperature for one hr.

To the thus activated 3,4-dichlorophenylacetic acid solution there was added dropwise a solution of 1.5 g (6.35 mmol) of 6-methylamino-7-(1-pyrrolidinyl)-1-oxaspiro[4.5]decane, prepared in part E above, in 10 ml of dry THF over a 20 min period. After complete addition the reaction mixture was stirred for 3 hr at room temperature to ensure complete reaction. The THF was removed in vacuo and the residue was distributed between 100 ml of diethyl ether and 100 ml of water. The ether phase was washed with 50 ml of brine solution, dried over magnesium sulfate and the solvent removed in vacuo. Chromatography of the residue on silica gel, eluting with 2.5% methanol (containing 10% ammonia/ethyl acetate) afforded 2.1 g (78% yield) of the above titled product. An ethereal solution of the free base product thus obtained was treated with a diethyl ether solution of hydrogen chloride. The resulting titled -amine.hydrochloride salt precipitate was recrystalized from a 1:1 v/v methanol:diethyl ether mixture to give the above titled amine product as the hydrochloride salt, mp 248°–251° C. The NMR and mass spectral analyses were consistent with this named titled product. The elemental analysis was as follows:

Anal. Calcd. for $C_{22}H_{31}N_2O_2.HCl.0.5H_2O$: C, 56.12; H, 6.85; N, 5.95, Cl, 22.59%. Found: C, 56.30; H, 6.85; N, 6.15, Cl, 22.20%.

The titled compound produced by the procedure of this example is a single epimer of unknown stereochemistry at $C_5$. The other $C_5$ epimer has mp 135°–137° C. and is named hereinbelow in Example 14.

EXAMPLE 5

Resolution of the dextro(+) and leavo(−) enantiomers of detailed Example 1 compounds Preparation of
(+)-(5α,7α,8β)-3,4-dichloro-N-methyl-N-[7-(1-pyrrolidinyl)-1-oxaspiro[4.5]dec-8-yl]benzeneacetamide
and
(−)-(5α,7α,8β)-3,4-dichloro-N-methyl-N-[7-(1-pyrrolidinyl)-1-oxaspiro[4.5]dec-8-yl]benzeneacetamide To a solution of 10.0 g (23.5 mmol) of the (±)-(5α,7α,8β)-3,4-dichloro-N-methyl-N-[7-(1-pyrrolidinyl)-1-oxaspiro[4.5]dec-8-yl]ben-zeneacetamide, prepared as described in Example 1 hereinabove, in 250 ml of methanol there was added 9.1 g (23.5 mmol) of di-p-toluoyl-d-tartaric acid and the resultant mixture was evaporated to dryness in vacuo. The resultant white solid was dissoled in a minimum volume of boiling methanol and enough diethyl ether was added to cause a slight clouding of the mixture. The slightly cloudy solution was allowed to stand at room temperature for 18 hr and the resultant crystals were collected to give 9.8 g of a white crystalline product. The crystalline product thus obtained was recrystallized twice from a 1:1 v/v mixture of methanol:diethyl ether to give 5.0 g of salt. This dextro-tartrate salt product was distributed between diethyl ether and 10% sodium hydroxide aqueous solution, the resulting liquid phases were separated, the ethereal phase was washed with brine, dried over magnesium sulfate and the solvent removed leaving 3.0 g of a white solid which was recrystallized from a diethyl ether/hexane (1:1 v/v) mixture to give 2.3 g of the essentially pure levo(−) isomer, mp 106°–107.5° C., $[\alpha]_{25}^D -6.13$, $[\alpha]_{436}^D -14.38$ (C=1.13,ethylacetate). The NMR spectrum was consistent.

Anal. Calcd. for $C_{22}H_{20}Cl_2N_2O_2$: C, 62.11; H, 7.11; N, 6.59; Cl, 16.67%. Found: C, 61.92; H, 7.16; N, 6.42; Cl, 16.83%.

The mother liquors from the above original crystallization was evaporated to dryness in vacuo and the residue was distributed between 10% sodium hydroxide aqueous solution and diethyl ether. The liquid phases were separated and the ethereal phase was washed with brine solution, dried over magnesium sulfate and the solvent removed in vacuo to leave 4.1 g of the above titled (±) free base as a white solid. The white free base (±) isomer mixture thus obtained was dissolved in 150 ml of methanol to which was added 3.9 g (9.6 mmol) of di-p-toluoyl-1-tartaric acid and the resultant solution was evaporated to dryness in vacuo. The resultant solid residue was recrystallized three times from a methanol/diethyl ether (1:1 v/v) mixture to give 3.2 g of salt. Treatment of this levo-tartrate salt as described above for the dextro-tartrate salt gave 2.0 g of the above-titled free levo(−) base which was recrystallized from diethyl ether/hexane (1:1 v/v) to give 1.55 g of the titled levo(−) isomer free base, mp 106.5°–107.5° C.; $[\alpha]_{25}^D +6.18$, $[\alpha]_{436}^{546} +14.51$. The NMR spectrum was identical to that for the dextro(+) isomer above.

Anal. Calcd. for $C_{22}H_{20}Cl_2N_2O_2$: C, 62.11; H, 7.11; N, 6.59; Cl, 16.67%.

EXAMPLE 6

General Procedure for the Acylation of (±)-(5α,7α,8β)-N-methyl-7-(1-pyrrolidinyl)-1-oxaspiro[4.5]decan-8-amine Preparation of (±)-(5α,7α,8β)-N-methyl-N-[7-(1-pyrrolidinyl)-1-oxaspiro[4.5]dec-8-yl]benzeneacetamide This example illustrates a general procedure for acylating the titled decan-8-amine to make compounds of this invention and, specifically, the production of (±)-(5α,7α,8β)-N-methyl-N-[7-(1-pyrrolidinyl)-1-oxaspiro[4.5]dec-8-yl]benzeneacetamide.

In a dried vessel containing stirring apparatus and pressure equalizing addition funnel equipment connected to de-aerating gas source such as nitrogen there is placed about 0.48 g (3.5 mmols) of the phenylacetic acid (or its equivalent of the selected ring-substituted phenylacetic acid) or benzoic acid or phenylalkanoic acid and 5 ml of THF (dried with 3A molecular sieves). To this stirred mixture is added, as a solid, 0.56 g (3.5 mmol) of 1,1'-carbonyldiimidazole in two batches. The mixture is stirred at room temperature for 45 min. To the resulting stirred activated acid mixture there is added dropwise 0.75 g (3.15 mmol) of the selected diamine, e.g., (±)-(5α,7α,8β)-N-methyl-7-(1-pyrrolidinyl)-1-oxaspiro[4.5]decan-8-amine (Example 1, Step H) in 10 ml of dry THF over a 10 min period. The resultant mixture is stirred at room temperature for 18 hr to ensure complete reaction. The THF is removed in vacuo and the residue is distributed between 30 ml of ethyl acetate and 20 ml of water. The organic liquid phase is separated, dried over magnesium sulfate and the solvent removed in vacuo to leave the acylated product of this invention, e.g., (±)-(5α,7α,8β)-N-methyl-[7-(1-pyrrolidinyl)-1-oxaspiro[4.5]dec-8-yl]benzeneacetamide, as a powdered product which is recrystallized, e.g., from acetonitrile to give the desired benzeneacetamide or benzamide product, e.g., 800 mg (71% yield) of the titled amino-amide, mp 123°–125° C.

EXAMPLE 7

1-Oxaspiro[4.5]dec-7-ene

This example illustrates a preferred procedure for preparing the compound of step E in Example 1 hereinabove.

In an oven dried 5 liter 3-neck round bottom flask equipped with two Dewar condensers, a glass covered magnetic stir bar and a positive nitrogen inlet there was condensed 1.75 liters of anhydrous ammonia flask was immersed in a dry ice/isopropanol bath during ammonia condensation). A solution of 136.19 g (1 mol) of 3-phenylpropanol (well known in the art) in 200 ml of dry diethy ether (cooled to −78° C. was added followed by a solution of 107.3 g (2.33 mol) of absolute ethanol in 200 ml of diethyl ether (cooled to −78° C.). To this solution there was added in small pieces, over a two hr period, 69.0 g (3 gram-atoms) of sodium metal (freed from mineral oil by washing with pentane). The first pieces caused vigorous exotherms and the rate of addition had to be carefully monitored. After the addition was complete, the reaction mixture (deep blue) was stirred for 18 hr without replenishing the coolant in the condenser.

The flask containing a white solid was cooled in an ice/water bath and 800 ml of ice cold water was added followed by 800 ml of diethyl ether. After all of the solid had dissolved the reaction mixture was transferred to a separatory funnel, the phases were separated and the ethereal phase was washed three times with 800 ml portions of water, once with brine solution, dried over magnesium sulfate and the solvent was removed leaving 143 g of crude 3-(1,4-cyclohexadienyl)propan-1-ol.

This crude 3-(1,4-cyclohexadienyl)propan-1-ol thus obtained was divided into two batches. Each batch was treated separately with 2.5 g of p-toluenesulfonic acid. The pressure was lowered to 12 mmHg and the pot immersed in an oil bath heated to 115° C. After about 0.3 hr distillation through a short vacuum jacketed vigreaux column at reduced pressure began and continued at a steady rate as cyclization proceeded. A total of 105.4 g (76% yield) of the 1-oxaspiro[4.5]dec-7-ene was obtained as a water white liquid, bp 79°–81° C. (12 mmHg). The NMR spectrum was identical to that for the same compound described in Example 1 above, step E.

EXAMPLE 8

(±)-(5α,7α,8β)-4-chloro-N-methyl-N-[7-(1-pyrrolidinyl)-1-oxaspiro[4.5]dec-8-yl]benzeneacetamide Employing the general procedure of Example 6, but using instead 4-chlorophenylacetic acid, there is produced in 89% yield the titled amino-amide, mp 109°-110° C., with the following elemental analysis.

Calcd for $C_{22}H_{31}ClN_2O_2$: C, 67.59; H, 7.99N, 7.17; Cl, 9.07%. Found: C, 67.48; H, 7.98; N, 7.05; Cl, 9.11%.

EXAMPLE 9

(±)-(5α,7α,8β)-4-bromo-N-methyl-N-[7-(1-pyrrolidinyl)-1-oxaspiro[4.5]dec-8-yl]benzeneacetamide Employing the general procedure of Example 6, but using instead 4-bromophenylacetic acid, there is produced in 93% yield the titled amino-amide, mp 120°-122° C., with the following elemental analysis.

Calcd for $C_{22}H_{31}BrN_2O_2$: C, 60.69; H, 7.18; N, 6.43; Br, 18.35. Found: C, 60.71; H, 7.16; N, 6.35; Br, 18.31.

EXAMPLE 10

(±)-(5α,7α,8β)-4-methoxy-N-methyl-N-[7-(1-pyrrolidinyl)-1-oxaspiro[4.5]dec-8-yl]benzeneacetamide Employing the general procedure of Example 6, but using instead 5-methoxyphenylacetic acid, there is produced in 73% yield the titled amino-amide, mp 110°-111° C., with the following elemental analysis.

Calcd for $C_{23}H_{34}N_2O_3$: C, 71.47; H, 8.87; N, 7.25. Found: C, 71.26; H, 8.97; N, 7.17.

EXAMPLE 11

(±)-(5α,7α,8β)-N,4-dimethyl-N-[7-(1-pyrrolidinyl)-1-oxaspiro[4.5]dec-8-yl]benzeneacetamide Employing the general procedure of Example 6, but using instead 4-methylphenylacetic acid there is produced in 74% yield the titled amino-amide, mp 95°-97° C., with the following elemental analysis.

Calcd for $C_{23}H_{34}N_2O_2$: C, 74.55; H, 9.25; N, 7.56. Found: C, 74.66; H, 9.22; N, 7.68.

EXAMPLE 12

(±)-(5α,7α,8β)-3-chloro-N-methyl-N-[7-(1-pyrrolidinyl)-1-oxaspiro[4.5]dec-8-yl]benzeneacetamide Employing the general procedure of Example 6, but using instead 3-chloroacetic acid there is produced in 70% yield the titled amino-amide, mp 91°-92° C., with the following elemental analysis.

Calcd for $C_{22}H_{31}N_2O_2Cl$: C, 67.59; H, 7.99; N, 7.17; Cl, 9.07. Found: C, 67.11; H, 7.98; N, 7.07; Cl, 8.98.

EXAMPLE 13

(±)-(5α,7α,8β)-N-methyl-4-nitro-N-[7-(1-pyrrolidinyl)-1-oxaspiro[4.5]dec-8-yl]benzeneacetamide Employing the general procedure of Example 6, but using instead 4-nitrophenylacetic acid there is produced in 71% yield the titled amino-amide as the monohydrochloride, hydrate, mp 156°-158° C., with the following elemental analysis.

Calcd for $C_{22}H_{31}N_3O_4 \cdot HCl \cdot H_2O$: C, 60.33; H, 7.36; N, 9.60; Cl, 8.06. Found: C, 59/86; H, 7.27; N, 9.61; Cl, 8.10.

EXAMPLE 14

(±)-(5ξ,6α,7β)-3,4-dichloro-N-methyl-N-[7-(1-pyrrolidinyl)-1-oxaspiro[4.5]dec-6-yl]benzeneacetamide Reacting 6,7-epoxy-1-oxaspiro[4.5]decane Isomer B from Example 4, Part C, as described for Isomer A in Example 4, Parts D, E, and F, there is produced the titled compound, mp 135°-137° C., which is the spiro epimer of the compound produced by the procedure of Example 4, Part F.

Calcd for $C_{22}H_{30}N_2Cl_2O_2$: C, 62.11; H, 7.11; N, 6.59; Cl, 16.67. Found: C, 62.06; H, 7.16; N, 6.54; Cl, 16.60.

EXAMPLE 15

(±)-(5α,7β,8α)-3,4-dichloro-N-methyl-N-[8-(1-pyrrolidinyl-1-oxaspiro[4.5]dec-7-yl]benzeneacetamide and its monohydrobromide, chloroform solvate

A.

(±)-(5α,7α,8β)-1-[7-(methylamino)-1-oxaspiro[4.5]dec-8-yl]pyrrolidine (Isomer A) and
(±)-(5α,7β,8α)-1-[7-(methylamino)-1-oxaspiro[4.5]dec-8-yl]pyrrolidine (Isomer B)

In a 25 ml round bottom flask, fitted with reflux condenser and magnetic stir bar, was placed 3.4 g (22.0 mmol) of epoxide Isomer A from Example 1, Part F, 1.72 g (24.0 mmol) pyrrolidine and 1 ml water. The mixture was heated with stirring under nitrogen at 70° C. for 2 hr. The reaction mixture was cooled to 0° in an ice water bath, 3.5 ml of 25% NaOH was added and the basic mixture was stirred in the cold for 15 min. The excess pyrrolidine was removed in vacuo. The aqueous residue was extracted two times with 50 ml methylene chloride. The combined organics were washed with 100 ml brine and dried (MgSO₄). The solvent was removed in vacuo and the residue distilled through a short path at reduced pressure to yield 4.3 g (87%, bp 100°-102° (0.05 mm), of amino-alcohol intermediate.

In an oven dried 100 ml r.b. flask, fitted with pressure equalizing addition funnel and magnetic stir bar, was placed 4.3 g of the above amino alcohol, 2.43 g (24.0 mmol) triethylamine and 25 ml of methylene chloride, and the mixture was cooled to 0° in an ice/water bath. To the stirred mixture was added 2.7 g (24.0 mmol) of methanesulfonyl chloride in 20 ml of methylene chloride dropwise over a 30 min period. The mixture was stirred in the cold another 30 min. The reaction mixture was washed with 50 ml water. The organic phase was dried (MgSO₄) and the solvent removed in vacuo to leave 6.0 g of crude mesylate product which was carried on without further purification.

The crude mesylate product from above was placed in a 100 ml round bottom flask, fitted with reflux condenser and magnetic stir bar, and 40 ml of 40% aqueous methyl amine. The mixture was heated at 70° for 2 hr. The excess methyl amine was removed in vacuo and the residue distributed between 150 ml of 10% sodium hydroxide and 150 ml methylene chloride. The aqueous phase was extracted with 150 ml. of methylene chloride. The combined organics were dried (MgSO₄) and the solvent removed in vacuo to leave 4.3 g of crude product. Gas chromatography indicated a 2:1 mixture of the titled Isomers A and B respectively. Chromatography of half of the crude on R.P.-2 silica gel, eluting with 2% NH₄OH (50% aqueous), 10% water, 88% CH₃CN (v:v:v) gave 1.6 g of Isomer A and 0.63 g of Isomer B (95%, based on crude product recover).

The HNMR of Isomer A was consistent with the named compound.

The HNMR of Isomer B was consistent with the above named Isomer B. The mass spec of Isomer B: m/3=238 (M+ 24.7%), 194 (78.5%), 126 (15.2%), 110 (100%), 97 (61.9%).

B.
(±)-(5α,7β,8α)-3,4-dichloro-N-methyl-N-[8-(1-pyrrolidinyl)-1-oxaspiro[4.5]-dec-7-yl]benzeneacetamide and its monohydrobromide In an oven dried 50 ml round bottom flask, fitted with pressure equalizing addition funnel and magnetic stir bar, was placed 0.59 g (2.9 mmol) 1,1'-carbonyldiimidazole. The resultant mixture was stirred at room temperature for 1 hr at which time 0.63 g (2.6 mmol) of diamine Isomer B from Part A above in 5 ml of THF was added dropwise over a 15 min period. The reaction mixture was stirred for 18 hr. The THF was removed in vacuo and the residue distributed between 30 ml ethyl ether and 30 ml of water, the ethereal phase was washed 2 times with 30 ml of water, 1 time 30 ml brine, dried (MgSO$_4$) and the solvent removed in vacuo. Chromatography on silica gel, eluting with 3% methanol (containing 10% ammonia)/97% ethyl acetate gave 0.8 g (75%) of the titled amino amide. The product was dissolved in ethyl ether and treated with an ethereal hydrogen bromide solution. The resultant precipitate was recrystallized from chloroform/hexane to yield the hydrobromide salt (mp 212°–215°).

High resolution mass spec: Calcd: 424.1692; Found: 424.1684.

Anal. Calc'd for C$_{22}$H$_{30}$N$_2$O$_2$Cl$_2$.HBr.0.5-H$_2$O.0.034CHCl$_3$: C, 50.95; H, 6.22; N, 5.39; Cl, 14.37; Br, 15.40. Found: C, 50.94; H, 6.13; N, 5.45; Cl, 14.37; Br, 16.20.

The HNMR (80 MHz, CDCl$_3$, free base) was consistent with the titled amino-amide. IR (Nujol): C=O 1640 cm$^{-1}$. Mass spec: M+ m/e 424, 426 (7.5 5.1%); 314, 316 (14.2, 9.3%), 207 (30.7%), 110 (100%), 97 (55.5%).

EXAMPLE 16
(±)-(5ξ,6α,7β)-3,4-dichloro-N-[7-(dimethylamino)-1-oxaspiro[4.5]dec-6-yl]-N-methylbenzeneacetamide

A.
(±)-(5ξ,6α,7β)-N$^6$-(phenylmethyl-N$^6$,N$^7$,N$^7$-trimethyl-1-oxaspiro[4.5]decan-6,7-diamine In a 100 ml round bottom flask, fitted with condenser and magnetic stir bar, was placed 3.8 g (25 mmol) of 5,6-epoxy-1-oxaspiro-[4.5]decane (Isomer B from Example 4 Part C), 4.5 g (37.5 mmol) benzyl(methyl)amine and 3 ml water. The mixture was heated with stirring at 90° for 3 days. The reaction mixture was cooled to 0° in an ice/water bath. To the cold mixture was added 4 ml of 25% sodium hydroxide solution. The basic mixture was extracted 2 times with 75 ml methylene chloride. The combined organics were dried (MgSO$_4$) and the solvent removed in vacuo. The excess benzyl(methyl)amine was removed by heating at 40° at high vacuo to leave 6.32 g (92%) of crude amino alcohol product that was used without further purification. The NMR spectrum was consistent with this amino alcohol intermediate.

In a 250 ml round bottom flask, fitted with pressure equalizing addition funnel, magnetic stir bar and positive nitrogen inlet, was placed 4.0 g (14.5 mmol) of the amino alcohol from above, 1.76 g (16.0 mmol) triethylamine and 40 ml methylene chloride. The mixture was cooled to 0° in an ice/water bath and 1.83 g (16.0 mol) of methanesulfonylchloride in 30 ml of methylene chloride was added dropwise over a 30 min period. The reaction mixture was stirred in the cold another 30 min. The solution was washed with 70 ml water, dried (MgSO$_4$) and the solvent removed in vacuo to leave 5.4 g of crude mesylate intermediate.

The crude mesylate was placed in a 100 ml round bottom flask, fitted with magnetic stir bar and condenser, along with 40 ml of 25% aqueous dimethylamine. The mixture was heated at 90° with stirring for 2 days. The mixture was cooled to 0° in an ice/water bath and treated with 2 ml 25% sodium hydroxide solution. The basic mixture was extracted 2 times with 50 ml methylene chloride. The combined organics were dried (MgSO$_4$) and the solvent removed in vacuo. Chromatography on silica gel eluting with 3% methanol (containing 10% NH$_3$)/97% ethylacetate yielded 2.4 g (55%) of the substituted diamine. The HNMR (80 MHz, CDCl$_3$) and mass spectral analyses were consistent with the subtitled diamine.

B.
(±)-(5ξ,6α,7β)-N$^6$,N$^7$,N$^7$-trimethyl-1-oxaspiro[4.5]-6,7-diamine

A mixture of 2.4 g (7.95 mmol) of the diamine from part A above, 2.4 g of 20% palladium on carbon and 100 ml of absolute ethanol was hydrogenated on a Parr apparatus at 40 psi for 4 hr. The reaction mixture was filtered through a filter aid, Celite ®. The filtered cake was thoroughly washed with ethanol and the combined filtrate and wash were concentrated in vacuo to leave 1.38 g (82%) of the subtitled diamine, which was used without further purification.

C.
(±)-(5ξ,6α,7β)-3,4-dichloro-N-[7-(dimethylamino)-1-oxaspiro[4.5]dec-6-yl]N-methylbenzeneacetamide In an oven-dried 100 ml round bottom flask, fitted with pressure equalizing addition funnel, magnetic stir bar and positive nitrogen inlet, was placed 800 mg (3.88 mmol) 3,4-dichlorophenylacetic acid and 5 ml THF (dried over 3A molecular sieves). To the mixture was added in two batches 630 mg (3.88 mmol) of 1,1'-carbonyldiimidazole and the mixture was stirred at room temperature for 1 hr. The system was purged with nitrogen and 750 mg (3.53 mmol) of the diamine from part B above in 5 ml THF was added dropwise over a 15 min period. The resultant mixture was stirred at room temperature for 18 hr. The THF was removed in vacuo, the residue was distributed between 30 ml ethyl acetate and 20 ml water. The organic phase was dried (MgSO$_4$) and the solvent removed in vacuo to leave a solid which was recrystallized from ethyl acetate to yield 1.15 g (82%) of the titled amino-amide, mp 131°–133°. HNMR (80 MHg, CDCl$_3$)δ=1.2–1.95 (m, 10H); 209 (s, 6H), 2.89 (s, 3H), 3.55–4.0 (m, 4H), 4.75 (d, 2H), 7.0–7.35 (m, 3H). IR (Nujol): C=O, 1634 cm$^{-1}$. Mass spec: m/e 398,400 (5.5, 3.6%, M+); 181 (33%); 168 (21%), 98 (18%); 84 (100%).

Anal. Calcd for C$_{20}$H$_{28}$Cl$_2$N$_2$O$_2$: C, 60.15; H, 7.07; N, 7.01; Cl, 17.76. Found: C, 59.92; H, 7.08; N, 6.93; Cl, 17.77.

The titled amino-amide thus produced is the C$_5$-epimer of the compound produced by the procedure of Example 17, Parts A–C.

EXAMPLE 17

(±)-(5ξ,6α,7β)-3,4-dichloro-N-[7-(dimethylamino)-1-oxaspiro[4.5]dec-6-yl]-N-methylbenzeneacetamide, and its monohydrochloride, hydrate

A.
(±)-(5ξ,6α,7β)-N⁶-(phenylmethyl-N⁶,N⁷,N⁷-trimethyl-1-oxaspiro[4.5]decan-6,7-diamine In a 250 ml of round bottom flask, fitted with condenser and magnetic stir bar, was placed 9.8 g (64 mmol) 5,6-epoxy-1-oxaspiro-[4.5]decan (Isomer A from Example 4, Part C), 11.57 g (95 mmol) benzyl(methyl)amine and 6 ml water. The mixture was heated, with stirring, at 70° for 18 hr. The reaction mixture was cooled to 0° in an ice/water bath. To the cold, stirred mixture was added, all at once, 6 ml of 25% sodium hydroxide solution. The basic mixture was extracted 2 times with 100 ml methylene chloride. The combined organic phases were dried (MgSO₄) and the solvent removed in vacuo. The excess benzyl(methyl)amine was removed by heating at 40° with high vacuum. The product was distilled through a short path at reduced pressure to give 15.7 g. (90%) of the amino alcohol intermediate product, bp 145°–150° (0.02 mm), as a liquid which crystallized at room temperature, mp 63°–65°.

Anal. Calcd. for $C_{17}H_{25}N_2O_2$: C, 74.14; H, 9.15; N, 4.09. Found: C, 74.34; H, 9.03; N, 5.09.

The NMR and Mass Spectral analyses were consistent with this aminoalcohol intermediate.

In a 100 ml oven dried round bottom flask, fitted with magnetic stir bar and pressure equalizing addition funnel, was placed 3.0 g (10.9 mmol) the amino alcohol from above, 1.32 g (12.0 mmol) triethylamine and 40 ml methylene chloride. The flask was cooled to 0° in an ice bath under nitrogen. To the cold, stirred solution was added dropwise over a 15 min period 1.38 g (12.0 mmol) methanesulfonyl chloride in 20 ml methylene chloride. The reaction mixture was stirred for another 30 min in the cold and washed with 50 ml water. The organic phase was separated, dried (MgSO₄) and the solvent removed in vacuo to leave 4.2 g of crude mesylate intermediate.

To half of the crude mesylate thus formed was added 15 ml of 25% aqueous dimethylamine and the mixture was heated and stirred in a sealed, stainless steel bomb at 110° for 24 hr. The reaction mixture was cooled to room temperature and treated with 1.5 ml 25% sodium hydroxide solution. The basic material was extracted two times with 50 ml methylene chloride. The combined organics were dried (MgSO₄) and the solvent removed in vacuo. The remaining mesylate was treated in like manner to give a combined yield of 3.3 g of crude product. The combined materials were chromatographed on silica gel, eluting with 1.5% methanol (containing 10% NH₃)/98.5% ethyl acetate to give 1.35 g (41%) of the subtitled diamine. The NMR spectrum was consistent with this benzylated diamine intermediate.

B.
(±)-(5ξ,6α,7β)-N⁶,N⁷,N⁷-trimethyl-1-oxaspiro[4.5]-decan-6,7-diamine

A mixture of 1.35 g (4.5 mmol) of the diamine from part A above, 1.35 g of 10% palladium on carbon and 100 ml absolute ethanol was hydrogenated at ca 40 psi for 18 hr. The reaction mixture was filtered through filter aid (Celite®) and the filter cake was washed thoroughly with ethanol. The combined filtrate and washings were concentrated in vacuo to leave 1 g (100% of debenzylated diamine product which was used without further purification.

C.
(±)-(5ξ,6α,7β)-3,4-dichloro-N-[7-(dimethylamino)-1-oxaspiro[4.5]dec-6-yl]-N-methylbenzeneacetamide and its monohydrochloride, hydrate In a 50 ml oven dried flask, fitted magnetic stir bar and pressure equalizing adition funnel, was placed 0.53 g (2.6 mmol) 3,4-dichlorophenylacetic acid and 5 ml of THF (dried over 3A molecular sieves). To the stirred mixture was added in two batches, as a solid, 0.42 g (2.6 mmol) 1,1'-carbonyldiimidizole. The apparatus was flushed with nitrogen and stirred at room temperature for 45 min at which time 0.5 g (2.4 mmol) of the diamine from part B above in 5 ml THF was added dropwise over a 15 min period. The reaction mixture was stirred at room temperature for 4 hr. The THF was removed in vacuo and the residue distributed between 30 ml ethyl acetate and 20 ml water. The organic phase was dried (MgSO₄) and the solvent in vacuo. Silica gel chromatography of the material, eluting with 2% methanol (containing 10% NH₃), 98% ethyl acetate gave 0.6 g (63%) of the titled free base as a colorless oil. The product was dissolved in ether and treated with an ethereal solution of HCl. The precipitate was collected and recrystallized from methanol/ether to yield the titled HCl salt, mp 190°–194°. HNMR (80 MHz, CDCl₃, free base)δ=1.2–1.90 (m, 10H), 2.18 (s, 6H), 2.98 (s, 3H), 3.55–3.75 (m, 4H), 4.5 ((d, 2H), 7.0–7.4 (m, 3H).

Anal. Calcd for $C_{20}H_{28}Cl_2N_2O_2 \cdot HCl \cdot 0.5\ H_2O$: C, 54.00; H, 6.46; N, 6.29; Cl, 23.91. Found: C, 54.16; H, 6.69; H, 6.39; Cl, 24.00.

IR: C=O 1645 cm⁻¹. Mass spec: m/e—398,400 (M+, 24.16%); 181 (81%); 168 (42%); 84 (100%).

The titled amino-amide thus produced is the C₅-epimer of the compound produced by the procedure of Example 16, Parts A–C.

EXAMPLE 18

(±)-(5α,7α,8β)-4-bromo-3-methoxy-N-methyl-N-[7-(1-pyrrolidinyl)-1-oxaspiro[4.5]dec-8-yl]benzamide The debenzylated diamine of Example 1, Step H is acylated with 3-bromo-4-methoxy benzoic acid by the general acylation procedure of Example 6 to produce in 60% yield the titled amino-amide, mp 156°–158° C., with the following elemental analysis.

Calcd for $C_{22}H_{31}N_2O_3Br$: C, 58.67; H, 6.71; N, 6.22; Br, 17.44. Found: C, 58.49; H, 6.71; N, 6.22; Br, 17.38.

EXAMPLE 19

(±)-(5α,7α,8β)-3-bromo-N-methyl-N-[7-(1-pyrrolidinyl)-1-oxaspiro[4.5]dec-8-yl]benzeneacetamide Employing the general procedure of Example 6 but using instead 3-bromophenylacetic acid there is produced the titled amino-amide, mp 93.5°–97° C., with the following elemental analysis.

Calcd for $C_{22}H_{31}BrN_2O_2$: C, 60.69; H, 7.18; N, 6.43; Br, 18.35. Found: C, 60.48; H, 7.33; N, 6.30; Br, 18.10.

EXAMPLE 20

(±)-(5α,7α,8β)-N-methyl-N-[7-(1-pyrrolidinyl)-1-oxaspiro[4.5]dec-8-yl]-3-(trifluoromethyl)benzeneacetamide Employing the general procedure of Example 6 but using instead 3-(trifluoromethyl)phenylacetic acid there is produced the titled amino-amide, which is isolated as the monohydrobromide, hemihydrate, mp 198°–201° C., with the following elemental analysis.

Calcd. for $C_{23}H_{31}N_2O_2F_3$ HBr 0.5 $H_2O$: C, 53.70; H, 6.47; N, 5.45; Br, 15.53. Found: C, 53.70; H, 6.33; N, 5.28; Br, 15.77.

EXAMPLE 21

($\pm$)-(5$\alpha$,7$\alpha$,8$\beta$)-N-methyl-2-nitro-N-[7-(1-pyrrolidinyl)-1-oxaspiro[4.5]dec-8-yl]benzeneacetamide Employing the general procedure of Example 6 but using instead 2-nitrophenylacetic acid there is produced in 63% yield the titled amino-amide, mp 124°–127° C. (from ethyl acetate), with the following elemental analysis.

Calc'd for $C_{22}H_{31}N_3O_4$: C, 65.81; H, 7.78; N, 10.47. Found: C, 65.52; H, 7.82; N, 10.40.

EXAMPLE 22

($\pm$)-(5$\alpha$,7$\alpha$,8$\beta$)-N-methyl-3-nitro-N-[7-(1-pyrrolidinyl)-1-oxaspiro[4.5]dec-8-yl]benzeneacetamide Employing the general procedure of Example 6 but using instead 3-nitrophenylacetic acid there is produced the titled amino-amide, which is isolated as the monohydrochloride, hemihydrate, mp 186°–189° C., with the following elemental analysis.

Calc'd for $C_{22}H_{31}N_3O_4$ HCl 0.5$H_2O$: C, 59.12; H, 7.44; N, 9.40; Cl, 8.16. Found: C, 59.17; H, 7.39; N, 9.23; Cl, 8.07.

EXAMPLE 23

($\pm$)-(5$\alpha$,7$\alpha$,8$\beta$)-N-methyl-4-nitro-N-[7-(1-pyrrolidinyl)-1-oxaspiro[4.5]dec-8-yl]benzeneacetamide and its monohydrochloride Employing the general procedure of Example 6 but using instead 4-nitrophenylacetic acid there is produced the titled amino-amide, mp 168°–171° C. (from diethyl ether-methanol), with the following elemental analysis.

Calcd for $C_{22}H_{31}N_3O_4$.HCl: C, 60.32; H, 7.36; N, 9.60; Cl, 8.10. Found: C, 59.86; H, 7.27; N, 9.61; Cl 8.06.

EXAMPLE 24

1-methanesulfonyl-1-azaspiro[4.5]dec-7-ene

In an oven dried 2 liter round bottom, three-neck flask, fitted with pyrex magnetic stir bar and Dewar condenser charged with dry ice/acetone, nitrogen inlet and cooled at $-78°$ in a dry ice/acetone bath, was condensed 600 ml of anhydrous ammonia. A solution of 100 ml dry ethyl ether, 56.26 g (1.22 mol) absolute ethanol and 50 g (0.37 mol) 3-phenyl-1-propylamine (Aldrich Chemical Co.) (cooled to $-78°$) was added and the dry ice/acetone bath removed. To this solution was added, in small pieces, over a 2 hr period 25.5 g (1.11 mol) of sodium metal (freed from mineral oil by washing in pentane) at a rate to maintain a gentle reflux of the ammonia. After complete addition the deep blue reaction mixture was stirred for 18 hr without replenishing the dry ice in the condenser.

The reaction flask, containing a white solid, was cooled with an ice/water bath and 500 ml of ice cold water was added followed by 600 ml of ether. After all the solids had dissolved the mixture was transferred to a separatory funnel and 150 ml of a saturated aqueous solution of ammonium chloride was added. The phases were mixed and separated. The aqueous was extracted with 400 ml ether. The combined ethereals were washed with brine, dried (MgSO$_4$) and the solvent removed in vacuo to leave 51 g of crude diene intermediate.

The crude product thus formed was placed in an oven dried 1 liter round bottom flask, fitted with magnetic stir bar, pressure equalizing additoin funnel and nitrogen inlet, along with 41.2 g (0.41 mol) triethylamine and 250 ml methylene chloride. The flask was cooled in an ice/water bath and 46.6 g (0.41 mol) methanesulfonylchloride in 150 ml methylene chloride was added dropwise over a 1 hr period to the stirred solution. The reaction mixture was stirred in the cold for another 45 min. The mixture was washed in 300 ml of water and dried (MgSO$_4$).

The mixture thus formed was diluted to 700 ml with methylene chloride and 6 ml of trifluoromethane sulfonic acid was added dropwise via syringe over a 10 min period and then stirred for 1 hr at room temperature. The mixture was washed 2 times with half saturated sodium bicarbonate solution, dried (MgSO$_4$) and the solvent removed in vacuo to leave 73 g of crude product. Silica gel chromatography, eluting with 40% ethylacetate/60% hexane, of 8 g of the crude afforded 6 g of the titled product as a white crystalline solid. The remaining crude was distilled through a short path at reduced pressure to yield 27.4 g (bp 126°–130° at 0.01 mm) of a colorless oil which crystallized upon standing at room temperature. The combined materials were recrystallized from hexane/ethylacetate to yield 33.4 g (42%) of the titled azacyclic olefin, mp 57°–59.5° C. The NMR spectrum was consistent with the sub-titled product.

Anal calcd for $C_{10}H_{17}NO_2S$: C, 55.78; H, 7.96; N, 6.51; S, 14.89. Found: C, 55.46; H, 7.94; N, 6.46; S, 14.69.

The mass spectrum analysis was also consistent with the sub-titled product.

EXAMPLE 25

1-thiaspiro[4.5]dec-7-ene

In an oven dried 2 liter round bottom three nesk flask, fitted with pyrex magnetic stir bar and Dewar condenser charged with dry ice/acetone nitrogen inlet and cooled to $-78°$ in a dry ice/acetone bath was condensed 500 ml anhydrous ammonia. A solution of 100 ml dry ethyl ether, 27.5 g (86.0 mmol) absolute ethanol and 40 g (26.0 mmol) 3-phenylpropylmercaptan (Aldrich Chemical Co.) (cooled to $-78°$) was added and the cooling bath was removed. To the stirred solution was added, in small pieces, over a 3 hr period, 23 g (1.05 mol) of sodium metal (freed from mineral oil by pentane wash) at a rate to maintain a gentle reflux of the ammonia. After complete addition the deep blue reaction mixture was stirred for 18 hr without replenishing the dry ice in the condenser.

The reaction flask, containing a white solid, was cooled with an ice/water bath and 500 ml of ice cold water was added followed by 500 ml Et$_2$O. After all the solids had dissolved the mixture was transferred to a separatory funnel, 200 ml of saturated NH$_4$Cl was added and the phases were mixed. The aqueous was extracted with 400 ml ether, the combined ethereals were washed with brine, dried (MgSO$_4$) and the solvent removed in vacuo to leave 40 g of a water white liquid. Gas chromatographic analysis showed the material to be a 4:1 mixture of product diene intermediate to starting material. The mixture was used without purification.

The crude material thus formed was treated with 2.5 g of p-toluenesulfonic acid and the pressure was lowered to 20 mm and the reaction flask was heated in an oil bath at 150°. After a short period distillation began through a vacuum jacketed vigreux column and continued as the cyclization proceeded, to give 28 g of material, bp=105°-109° (20 mm) which by G.C. analysis consisted of an 11:2:1 mixture of the titled cyclized olefin. This fraction was redistilled though a vacuum jacketed vigreux volumn at reduced pressure to collect 15 g (38%) of 1-thiaspiro[4.5]dec-7-ene as a colorless liquid, bp 118°-125° (32 mm). The NMR was consistent.

Other representative examples of compounds within the scope of this invention which can be prepared by procedures described in this specification are the cis and trans isomers of:

a. N-methyl-N-[7-(1-pyrrolidinyl)-1-azaspiro[4.5]dec-8-yl]-4-trifluoromethylbenzeneacetamide
b. N-methyl-N[8-(1-pyrrolidinyl)-1-thiaspiro[4.5]dec-7-yl]-3-trifluoromethylbenzeneacetamide
c. 4-chloro-N-methyl-N-[7-(1-pyrrolidinyl)-1-[N-ethylazaspiro[4.5]dec-8-yl]benzamide
d. 4-fluoro-N-methyl-N-[7-(1-pyrrolidinyl)-1-benzoylazaspiro[4.5]dec-8-yl]benzamide
e. 4-bromo-N-methyl-N-[7-(1-piperidinyl)-1-(3,4-dichlorobenzoyl)-1-azaspiro[4.5]undec-8-yl]benzeneacetamide
f. N-[8-(1-azetidinyl)-1-acetyl-1-azaspiro[4.5]dec-7-yl]-N-methyl-4-nitrobenzamide
g. N-[8-amino-1-(1-propionyl)-1-azaspiro[4.5]dec-7-yl]-N-methyl-2-chlorobenzeneacetamide
h. 3-amino-N-methyl-N-[8-(1-pyrrolidinyl)-1-butanoyl-1-azaspiro[4.5]-dec-7-yl]benzeneacetamide
i. N-[8-(ethylamino)-1-thiaspiro[4.5]dec-7-yl]-4-methoxy-N-methylbenzamide, 1,1-dioxide
j. 3-hydroxy-N-[7-(isopropylamino)-1-thiaspiro[4.5]dec-8-yl]N-methylbenzeneacetamide, 1-oxide
k. N-[7-(diethylamino)-1-thiaspiro[4.5]dec-8-yl]-N,2-dimethylbenzeneacetamide
l. N-[8-(1-azetidinyl)-1-oxaspiro[4.5]dec-7-yl]-N-methyl-[1,1'-biphenyl]-3-acetamide
m. N-[8-(dimethylamino)-1-azaspiro[4.5]dec-7-yl]-3-methanesulfonyl-N-methylbenzamide
n. 3-ethoxycarbonyl-N-methyl-N-[7-(1-piperidinyl)-1-propyl-1-azaspiro[4.5]dec-8-yl]benzamide
o. 3,4-dichloro-N-ethyl-N-[8-(1-pyrrolidinyl)-1-oxaspiro[4.5]-dec-7-yl]benzeneethanethioamide
p. 4-bromo-N-methyl-N-[8-(1-pyrrolidinyl)-1-[N-(4-methylbenzoyl)-1-azaspiro[4.4]non-7-yl]benzenecarbothioamide
q. 3,4-dichloro-N-methyl-N-[7-(1-pyrrolidinyl)-1-N-(4-methoxybenzoyl)azaspiro[4.5]dec-8-yl]benzeneethanethioamide
r. 4-bromo-N-methyl-N-[7-(1-pyrrolidinyl)-1-N-(4-hydroxybenzoyl)-azaspiro[4.5]dec-8-yl]benzenecarbothioamide
s. 3,4-dichloro-N-methyl-N-[8-(1-pyrrolidinyl)-1-thiaspiro[4.5]dec-7-yl]benzeneethanethioamide, 1,1-dioxide
t. 4-ethoxycarbonyl-N-methyl-N-[8-(1-pyrrolidinyl)-1-N-methylazaspiro[4.5]dec-7-yl]benzenecarbothioamide
u. 4-methanesulfonyl-N-methyl-N-[7-(1-pyrrolidinyl)-1-oxaspiro[4.5]dec-8-yl]benzeneethanethioamide
v. 4-azida-N-(1-n-propyl)-N-[7-(1-pyrrolidinyl)-1-oxaspiro[4.5]-dec-8-yl]benzeneethanethioamide
w. 4-phenyl-N-methyl-N-[8-(1-pyrrolidinyl)-1-thiaspiro[4.5]dec-7-yl]benzeneethanethioamide
x. 4-cyano-N-methyl-N-[7-(1-pyrrolidinyl)-1-oxaspiro[4.5]dec-8-yl]benzenecarbothioamide
y. 4-amino-N-methyl-N-[7-(1-pyrrolidinyl)-1-oxaspiro[4.5]dec-8-yl]benzenecarbothioamide
z. 4-acetoxy-N-ethyl-N-[8-(1-pyrrolidinyl)-1-oxaspiro[4.5]dec-7-yl]benzenecarbothioamide
aa. 4-acetamido-N-ethyl-N-[7-(N,N-dimethylamino)-1-oxaspiro-[4.5]dec-8-yl]benzamide
bb. 3,4-dichloro-N-methyl-N-[8-(1-pyrrolidinyl)-1-oxaspiro[5.5]-undec-9-yl]benzeneacetamide
cc. 3,4-dichloro-N-methyl-N-[8-(1-pyrrolidinyl)-1-aza[5.5]undec-9-yl]benzeneacetamide
dd. 3,4-dichloro-N-methyl-N-[8-(1-pyrrolidinyl)-1-thia[5.5]undec-9-yl]benzeneacetamide and its 1-oxides and 1,1-dioxides
ee. 3,4-dichloro-N-[7-(1-pyrrolidinyl)-1-oxaspiro[4.5]-dec-8-yl]benzeneacetamide.
ff. 4-bromo-N-[7-(1-pyrrolidinyl)-1-oxaspiro[4.5]dec-8-yl]benzeneacetamide
gg. 3-chloro-N-[7-(1-pyrrolidinyl)-1-oxaspiro[4.5]dec-8-yl]benzeneacetamide

EXAMPLE 26

(5α,7α,8β)-(±)-3,4-Dichloro-N-methyl-N-[7-(1-pyrrolidinyl)-1-oxaspiro[4.5]dec-8-yl]benzeneacetamide, methanesulfonate For reasons relating to various chemical and physical properties, as they may affect pharmaceutical drug formulation compounding, such as ease of being able to obtain profile drug (i.e., good elemental analyses, low solvent content, etc., melting point, water solubility properties, hygroscopic properties, chemical stability, and the like), the methanesulfonate salt form of the compound of detailed Example 1 above, has been selected for more advanced testing. The following description sets forth two methods for preparing the above-named methanesulfonate salt.

Method A: To a solution of 5.0 g (11.7 millimoles) of (5α,7α,8β)-(±)-3,4-dichloro-N-methyl-N-[7-(1-pyrrolidinyl)-1-oxaspiro[4.5]dec-8-yl]benzeneacetamide in 100 ml of dry methanol cooled in an ice-water bath there was added dropwise 11.7 ml (11.7 millimoles) of a 1.0 M solution of methanesulfonic acid in methanol. After the addition was complete the solvent was removed in vacuo leaving a white foam. The crude product was recrystallized from methanol/diethyl ether to give 5.1 g (83 percent yield) of white crystals of the titled salt, m.p. 210°-214° C.

Anal. Calcd. for $C_{23}H_{34}Cl_2N_2O_5S$: C, 52.97; H, 6.57; N, 5.37; C, 13.60; S, 6.15. Found: C, 52.62; H, 6.62; N, 5.41; C, 13.64; S. 6.08.

Method B: A 1130 g (2.66 mole) batch of (5α,7α,8β)-(±)-3,4-dichloro-N-methyl-N-[7-(1-pyrrolidinyl)-1-oxaspiro[4.5]dec-8-yl]benzeneacetamide was dissolved in 5 liters of methylene chloride and filtered into a clean, dry 12 liter reaction vessel equipped with a mechanical stirrer nitrogen inlet, thermometer, and a 1 liter dropping funnel. (Footnote 1)

The solution was cooled to about 15° C. in an ice-water bath and a solution of 256 g (173 ml, 2.66 M) of methanesulfonic acid in 500 ml of methylene chloride was added over about 1 hour and stirred for about 30 minutes (Footnote 2).

The addition funnel was replaced with vacuum distillation apparatus and most of the methylene chloride was removed under vacuum pressure at about 40° C. (Footnote 3).

Then 600 ml of methanol was added to the residue and sufficient time was allowed, with stirring, for solution to become complete.

The resulting solution was cooled to 20° C. and diluted by the slow addition of 6 liters of diethyl ether over 2 hours.

The resulting mixture was stirred overnight at room temperature under nitrogen (Footnote 4).

The resulting mixture was filtered and the solids were washed with 2 liters of diethyl ether. The filtered crystals of the titled methanesulfonate salt were air-dried for 3 hours and then dried in vacuo at 50° C. for 20 hours (Footnote 5).

Footnotes:

(1) The $(5\alpha,7\alpha,8\beta)$-$(\pm)$-3,4-dichloro-N-methyl-N-[7-(1-pyrrolidinyl)-1-oxaspiro[4.5]dec-8-yl]benzeneacetamide free base was contaminated with an inorganic solid. Actually, 1230 g of material was used of which 1130 g was the desired free base. The inorganic solid was filtered away and apparently caused no difficulty with the subsequent methanesulfonate salt formation.

(2) The pH is helpful to determine if enough methanesulfonic acid has been added. When addition is complete a pH of 5 to 7 should be observed on moist pH litmus paper. If a large excess of methanesulfonic acid has been added, decomposition in the concentration step may be a problem.

(3) A final volume of about 2 liters of residual material, with some crystallization, was obtained.

(4) The methanesulfonate salt of the titled aminoamide crystallizes slowly and best yields are obtained with overnight stirring.

(5) If methylene chloride is present in the final solids (as determined by NMR analysis), a recrystallization from methanol/diethyl ether may be required.

(a) Dissolve the crystalline material in 3 to 4 ml/g of methanol, (b) Dilute the resulting solution with 25 ml/g of diethyl ether, (c) Stir the mixture for several hours, filter, and dry as described above.

Compounds of formula (I) where the cycloalkyl ring (the ring that contains the $-(CH_2)_p-$ and $-(CH_2)_n-$ moieties) contains 5 or 7 ring carbon atoms are also included within the scope of this invention. Such 5 or 7 ring carbon atom cycloalkyl ring compounds are those wherein $p+n+3$ equals 5 or 7. In the process Schemes X to XII, provided herewith, r is 1 or 2, and $p+n+3$ carbon atoms equals 5 or 7 when $j+k$ equals 2 or 4.

With respect to chemical formula Schemes X to XII, the following comments are offered:

SCHEME X

The process of Scheme X can be used to prepare the 1-oxaspiroolefin intermediate compounds which ring olefin compounds are used to prepare compounds of this invention wherein Z (in the generic compound per se Formula (I) is oxygen and $p+n+3$ is equal to 5 or 7, so that the cycloaliphatic ring containing p and n is a five- or seven-membered carbon ring. In Scheme X, $J+k$ is equal to 2 or 4, and the chemical process steps are described as follows:

1a. The protected bromoalkanol (shown as an acetal) is metalated (i) with lithium wire at $-20°$ to 23° C. in diethyl ether (Et$_2$O) or THF, or (ii) with tertiary butyllithium at $-78°$ C. in Et$_2$O or THF.

1b. To the resulting lithium reagent from step 1(a) is added the selected C$_5$ or C$_7$ cycloalkenone in Et$_2$O or THF at $-78°$ C. to reflux, to form the cyclic compound shown at the beginning of Step 2.

2. The acetal protecting group is removed by mild acid hydrolysis with:

(a) an ion exchange resin (e.g., Dowex-50-WX8) in methanol at about 23° C. (room temperature), or (b) with an ethanol/water/hydrochloric acid (57.6/38.6/3.8 v/v/v) mixture at about 23° C., to form the di-hydroxy (—OH) compound shown at the beginning of Step 3.

3. The di-hydroxy compound from Step 2 is subjected to spirocyclization: (i) for all values of j and k by treatment with methanesulfonyl chloride and two equivalents of triethylamine in methylene chloride at about 0° to 41° C., or (ii) when one of j and k is zero using acids such as p-toluenesulfonic, hydrochloric, or trifluoromethanesulfonic acid with or without solvents such as methanol, ethanol, THF or DMF.

SCHEME XI

The chemical process of Scheme XI is used to prepare the 1-oxaspiro olefin intermediate compound used to prepare compounds of this invention where Z (in the generic compound per se Formula I) is NR$_3$ and $p+n+3$ is equal to 5 or 7, so that the cycloaliphatic ring, containing p and n, is a five- or seven-membered carbon ring. In Scheme XI, $j+k$ is equal to 2 or 4, and the chemical process steps are described as follows:

1a. The sulfonyl-protected bromo-amine is metalated (i) with lithium wire at $-20°$ to 23° C. in Et$_2$O or THF, or (ii) with tertiary butyllithium at $-78°$ C. in Et$_2$O or THF.

1b. To the resulting lithium reagent, from Step 1a, there is added the appropriate C$_5$ or C$_7$-cycloalkenone in Et$_2$O or THF at $-78°$ C. to reflux, to form the cyclic compound shown at the beginning of Step 2.

2. The resulting hydroxy-olefinic compound from Step 1 is subjected (i) to acid catalyzed azaspirocyclization when one of j and k is zero using acids such as p-toluenesulfonic, hydrodbromic or trifluoromethanesulfonic acid or the like, with or without a solvent such as methanol, ethanol, THF or benzene, or (ii) for all values of j and k to treatment with methanesulfonyl chloride and two equivalents of triethylamine in methylene chloride at about 0° to 41° C., to form the sulfonyl protected aza-spiro-bicyclic olefin shown at the beginning of Step 3.

3. The N-protected-aza-spiro bicyclic olefin, is subjected to reductive cleavage of the methanesulfonyl-protecting group at the desired stage in the synthesis, as described in Steps 3 and 4 of Scheme V, hereinabove.

SCHEME XII

The process of Scheme XII can be used to prepare the 1-thiaspiroolefin intermediate compounds used to make the compounds of this invention of Formula I wherein Z is S, SO or SO$_2$ and $p+n+3$ is equal to 5 or 7, so that the resulting cycloaliphatic ring containing p and n is a five- or seven-membered carbon ring. In Scheme XII $j+k$ is equal to 2 or 4, and the steps are described as follows:

1a. The protected bromothiol is metalated (i) with lithium wire at $-20°$ to 23° C. in Et$_2$O or THF, or (ii) with tertiary butyllithium at $-78°$ C. in Et$_2$O or THF.

1b. To the resulting lithium reagent prepared in Step 1a, there is added the appropriate C$_5$ or C$_7$-cycloalkenone in Et$_2$O or THF at $-78°$ C. to reflux, to form the cyclic compound shown at the beginning of Step 2.

2. The mono-thio acetal protecting group is cleaved by (a) stirring the sulfur-protected cyclic compound in methanol solution in the presence of an acidic resin such as Dowex-50-WX8 resin or other acid catalyst such as hydrochloric, p-toluenesulfonic or hydrobromic acid in acetic acid, methanol or ethanol, or (b) treating the sulfur-protected cyclic compound with boron trifluoride etherate in acetic acid, to form the cyclic olefinic hydroxy thiol compound shown at the beginning of Step 3.

3. The cyclic olefinic hydroxy thiol compound is subjected (i) to acid catalyzed spirothiacyclization when one of j and k is zero using acids such as p-toluenesulfonic, hyrochloric or trifluoromethanesulfonic acid with or without solvents such as methanol, ethanol, THF or DMF, or (ii) for all values of j and k to treatment with methanesulfonyl chloride and two equivalents of triethylamine in methylene chloride at about 0° to 41° C.

The cyclized olefins produced by the processes of Schemes X to XII are further reacted by epoxidation, epoxide opening, mesylate formation, diamine formation, amine protection, amine-acylation, and optional sulfur oxidation steps as set forth in Scheme I, Steps 9 to 12, and Scheme IV, Steps 7 and 8, hereinabove.

The cycloalkenone compounds used in the various process scheme outlines shown hereinabove are commercially available or at least known compounds. Thus, 3-cyclopentenone, a compound where j is 1 and k is 1, is described in the J. Org. Chem., 32, 3148 (1967).

The 2-cyclopentenone, a compound where j is 0 and k is 2, is commercialy available.

2-Cycloheptenone, where j is 0 and k is 4, is commercially available.

3-Cycloheptenone, where j is 1 and k is 3, is disclosed in Tetrahedron, Suppl. 8, Part 1, p. 105 (1966).

4-Cycloheptenone where j is 2 and k is 2, is described in J. Am. Chem. Soc, 94, (1972), p. 6026.

Thus, this invention includes compounds of Formula I, having expanded definitions of the variables set forth hereinabove, for the compounds of Formula I wherein the wavy line bonds between the nitrogens and the cycloaliphatic ring carbon atoms indicate a cis or trans relationship of the two nitrogen-containing groups at positions 1 and 2 of the cycloaliphatic ring, p is a whole number integer 0, 1, 2, 3, 4 and n is a whole number integer 0, 1, 2, 3, or 4 so that the resulting cycloaliphatic ring containing p and n has 5, 6 or 7 carbons;

m is 3 or 4;

A is a single chemical bond (—), —(CH$_2$)$_q$—where q is a whole number integer 1 to 4 or —CH(CH$_3$)—;

X and Y are independently selected from the group consisting of hydrogen, a halogen having an atomic number of from 9 to 35, trifluoromethyl, nitro, methoxy, hydroxy, azido, C$_1$ to C$_3$-alkyl, phenyl, methanesulfonyl, cyano, amino, C$_1$ to C$_3$-alkoxycarbonyl, C$_1$ to C$_3$-alkanoyloxy, C$_1$ to C$_3$-carboxyacylamino (—NHC(O)R$_4$ wherein R$_4$ is hydrogen or C$_1$ to C$_2$-alkyl);

R is hydrogen or C$_1$ to C$_3$-alkyl;

R$_1$ and R$_2$, taken separately, are each hydrogen, C$_1$ to C$_3$-alkyl or allyl;

R$_1$ and R$_2$, taken together with the nitrogen to which they are bonded, complete a ring selected from the group consisting of azetidinyl, pyrrolidinyl, piperidinyl, pyrrolyl, 3-pyrrolin-1-yl

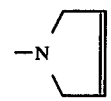

3-azabicyclo[3.1.0]hexan-3-yl

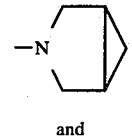

and 3-azabicyclo[3.2.0]heptan-3-yl

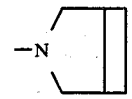

E is oxygen or sulfur,

Z is selected from the group consisting of oxygen (—O—), —NR$_3$—, bivalent sulfur (—S—), sulfinyl (—S(O)—) and sulfonyl (—S(O)$_2$—);

R$_3$ is hydrogen, C$_1$ to C$_3$-alkyl, benzoyl, X- and Y-ring substituted benzoyl, C$_2$ to C$_4$-alkanoyl (—C(O)—C$_1$ to C$_3$-alkyl);

provided that when p is 2, n is 1, m is 3, A is (CH$_2$)$_q$ where q is 1, R$_1$ is methyl, R$_1$ and R$_2$ are taken together with the nitrogen to which they are bonded to complete a pyrrolidinyl ring, E is oxygen, Z is oxygen, and the relative stereochemistry is (5α,7α,8β), then X and Y taken together on the phenyl ring cannot be chlorine on the 2- and 4-positions on the phenyl ring.

Pharmacologically acceptable salts of such compounds of Formula I are also part of this invention.

This expanded definition of the group of compounds thus includes all of the C$_5$ to C$_7$-cycloaliphatic ring compounds, (p+n+3=5 or 7), and an expanded list of —NR$_1$R$_2$ amino groups.

All of the compounds of Formula I are characterized by their containing the new mono-oxy, thia- or aza-ring structure attached to the C$_5$ to C$_7$-cycloaliphatic ring and as asymmetric carbon atom of the cycloaliphatic ring which features are not found in prior art compounds of which we are aware.

The compounds of Formula I or their acid addition salts in their crystalline state may sometimes be isolated from their reaction mixture as solvates, as indicated above. Also, as with the cyclohexyl compounds described above, the cyclopentyl and cycloheptyl ring compounds contain at least three asymmetric carbon atoms, each of which possess R- and S- configurations, and possess the same possible cis and trans orientation considerations as is indicated above for the cyclohexyl compounds.

After preparing the required C$_5$ or C$_7$-cycloaliphatic ring containing olefin intermediates, and the respective diamine therefrom, the new Formula Ia compounds are prepared by acylation procedures described hereinabove. If desired, the respective d- and l-optical isomers can be prepared or separated by methods described above.

Using the procedures described above, the following compounds are prepared:

hh. (±)-(5ξ,7α,8β)-3,4-dichloro-N-methyl-N-[7-(1-pyrrolidinyl)-1-azaspiro[4.5]dec-8-yl]benzeneacetamide, mp 94°–96° C., ii. (±)-(5ξ,7α,8β)-3,4-dichloro-N-methyl-N-[7-(1-pyrrolidinyl)-1-azaspiro[4.5]dec-8-yl]benzeacetamide, the 5-epimer of the compound named immediately above, fumarate, mp 125°–131° C., jj. (±)-(5α,7α,8β)-N-methyl-N-[7-(1-pyrrolidinyl)-1-oxaspiro-[4.5]dec-8-yl]benzenepropanamide, mp 116°–118° C., kk. (±)-(5ξ,7α,8β)-3,4-dichloro-N-methyl-N-[8-(1-pyrrolidinyl)-1-azaspiro[4.5]dec-7-yl]benzeneacetamide, mp 97°–99° C., ll. (±)-(5ξ,7α,8β)-3,4-dichloro-N-methyl-N-[8-(1-pyrrolidinyl)-1-azaspiro[4.5]dec-7-yl]benzeneacetamide, 5-epimer of the compound named immediately above, mp 83°–85° C., mm. (±)-(5ξ,7α,8β)-4-bromo-N-methyl-N-[7-(1-pyrrolidinyl)-1-aza-spiro[4.5]dec-8-yl]benzamide, mp 124°–125.5° C., nn. (±)-(5α,7α,8β)-N-methyl-N-[7-(1-pyrrolidinyl)-1-oxaspiro-[4.5]-dec-8-yl]benzenebutanamide, mp 74.5°–77° C., oo. (±)-(5ξ,7α,8β)-3,4-dichloro-N-methyl-N-[7-(1-pyrrolidinyl)-1-thiaspiro[4.5]dec-8-yl]benzeneacetamide, 1,1-dioxide, mp 130°–132° C., pp. (±)-(5ξ,7α,8β)-3,4-dichloro-N-methyl-N-[8-(1-pyrrolidinyl)-1-thiaspiro[4.5]dec-7-yl]benzeneacetamide, 1,1-dioxide, mp 147°–148° C., qq. (±)-(5ξ, 7α,8β)-4-bromo-N-methyl-N-[8-(1-pyrrolidinyl)-1-azaspiro[4.5]dec-7-yl]benzamide, mp 118°–121° C., rr. (±)-(5ξ,7α,8β)-3,4-dichloro-N-methyl-N-[7-(1-pyrrolidinyl)-1-thiaspiro[4.5]dec-8-yl]benzeneacetamide, mp 118.5°–120° C., ss. (±)-(5ξ,7α,8β)-4-bromo-N-methyl-N-[7-(1-pyrrolidinyl)-1-thiaspiro[4.5]dec-8-yl]benzamide, mp 136°–137° C., tt. (±)-(5ξ,7α,8β)-3,4-dichloro-N-methyl-N-[8-(1-pyrrolidinyl)-1-thiaspiro[4.5]dec-7-yl]benzeneacetamide, mp 104°–106° C., uu. (±)-(5ξ,7α,8β)-4-bromo-N-methyl-N-[8-(1-pyrrolidinyl)-1-thiaspiro[4.5]dec-7-yl]benzamide, mp 136°–140° C., vv. 3,4-dichloro-N-methyl-N-[7-(1-pyrrolyl)-1-oxaspiro[4.5]dec-8-yl]benzeneacetamide, ww. 4-bromo-N-methyl-N-[7-(1-piperidinyl)-1-oxaspiro-[4.5]-dec-8-yl]benzamide, xx. 3-chloro-4-methoxy-N-methyl-N-[7-(3-pyrrolin-1-yl)-1-oxaspiro[4.5]dec-8-yl]benzeneacetamide, yy. 4-trifluoromethyl-N-methyl-N-[7-(3-azabicyclo[3.1.0]hexan-3-yl)-1-oxaspiro[4.5]dec-8-yl]benzenepropanamide, zz. 3,4-dichloro-N-methyl-N-[7-(3-azabicyclo-[3.2.0]-heptan-3-yl]-1-oxaspiro[4.5]dec-8-yl]benzeneacetamide, aaa. 3,4-dichloro-N-methyl-N-[7-(1-pyrrolidinyl)-1-oxaspiro[4.6]-undec-6-yl]benzeneacetamide, bbb. 3,4-dichloro-N-methyl-N-[8-(1-pyrrolidinyl)-1-oxaspiro[4.6]-undec-7-yl]benzeneacetamide, ccc. 3,4-dichloro-N-methyl-N-[9-(1-pyrrolidinyl)-1-oxaspiro[4.6]-undec-8-yl]benzeneacetamide, ddd. 3,4-dichloro-N-methyl-N-[7-(1-pyrrolidinyl)-1-oxaspiro[4.6]-undec-8-yl]benzeneacetamide, eee. 3,4-dichloro-N-methyl-N-[6-(1-pyrrolidinyl)-1-oxaspiro[4.6]undec-7-yl]benzeneacetamide, fff. 3,4-dichloro-N-methyl-N-[6-(1-pyrrolidinyl)-1-oxaspiro[4.4]non-7-yl]benzeneacetamide, ggg. 3,4-dichloro-N-methyl-N-[7-(1-pyrrolidinyl)-1-oxaspiro[4.4]non-8-yl]benzeneacetamide, hhh. 3,4-dichloro-N-methyl-N-[7-(1-pyrrolidinyl)-1-oxaspiro[4.4]non-6-yl]benzeneacetamide, iii. (±)-(5ξ,7α,8β)-3,4-dichloro-N-methyl-N-[7-(1-pyrrolidinyl)-1-thiaspiro[4.5]dec-8-yl]benzeneacetamide, mp 129°–132° C., and the like.

The expanded group of compounds of Formula I are useful for the same uses set forth above for the previous, above Formula I compounds. The compound of Example 1, as its methanesulfonate salt, has been selected for advanced analgesic testing.

(A) GENERAL CHEMICAL STRUCTURES

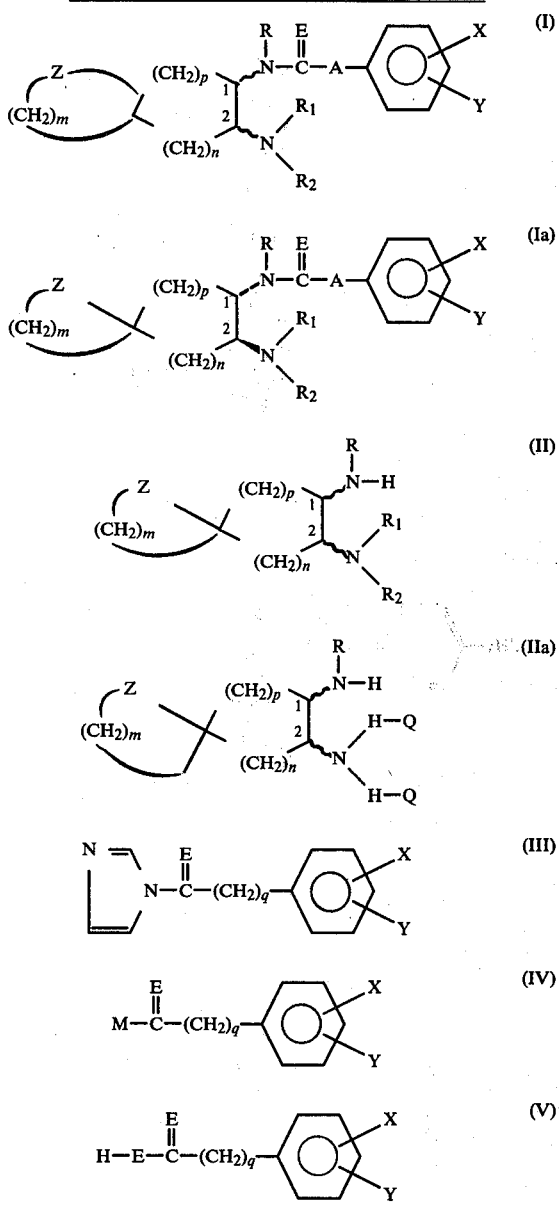

SCHEME I(Z=O)

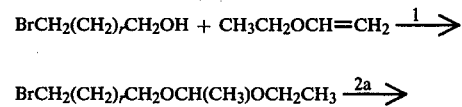

-continued
SCHEME I (Z=O)
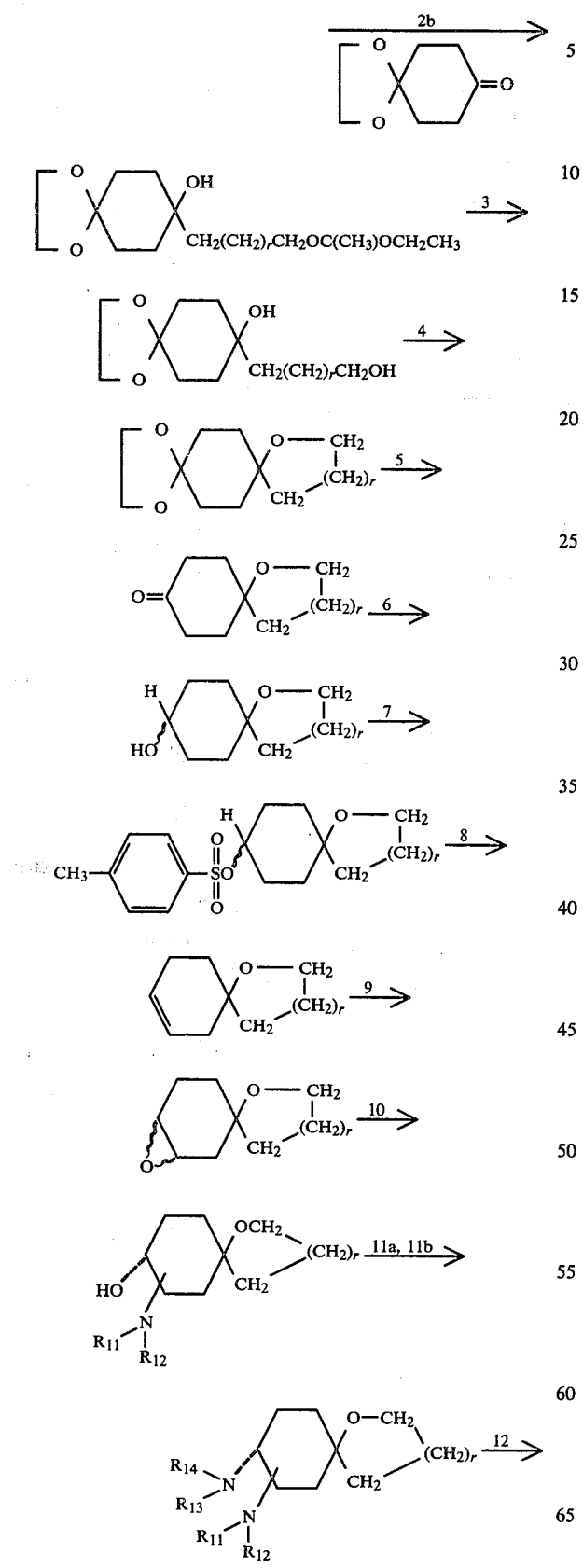
SCHEME II (Z=N—R³)
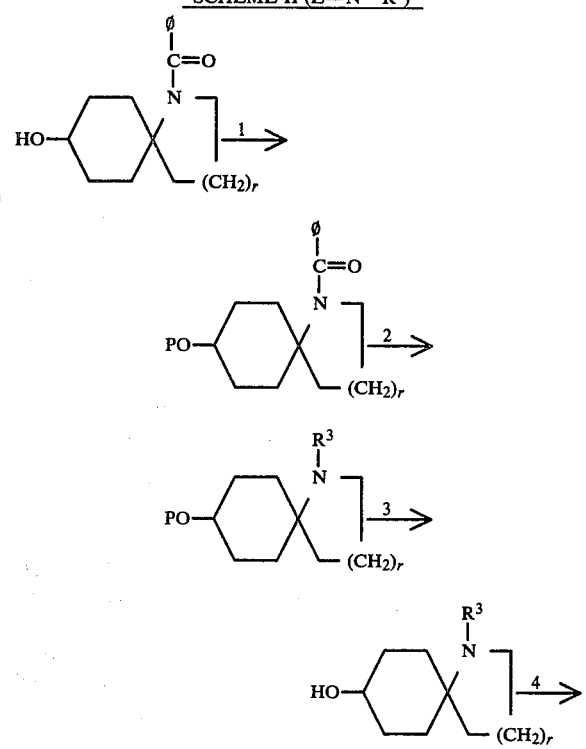
SCHEME III
Preparation of 1-aza[5.5]undeca-9-ol
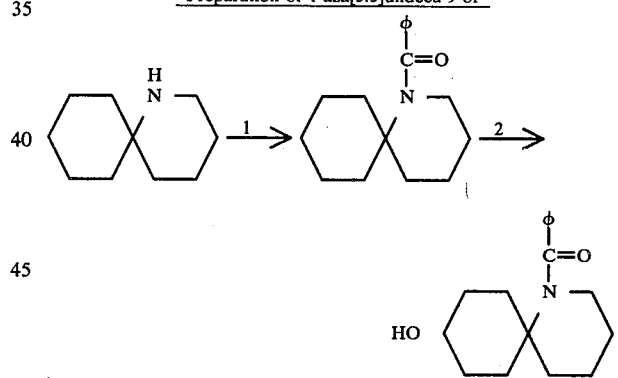
¹benzoyl chloride, pyridine
²sporotrichium sulfurescens V. Beyma (ATCC 7159)
SCHEME IV (Z=S, SO, or SO₂)
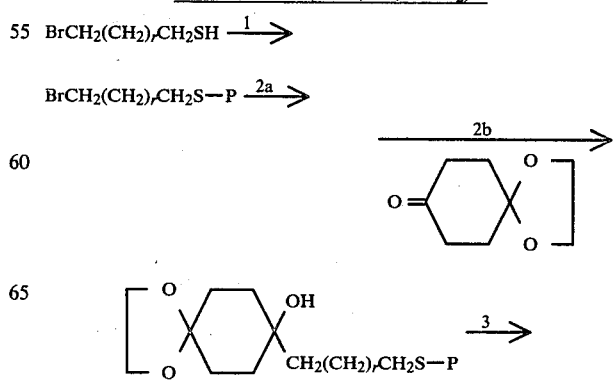

SCHEME IV (Z=S, SO, or SO₂) -continued
SCHEME VII
SCHEME VIII
SCHEME V
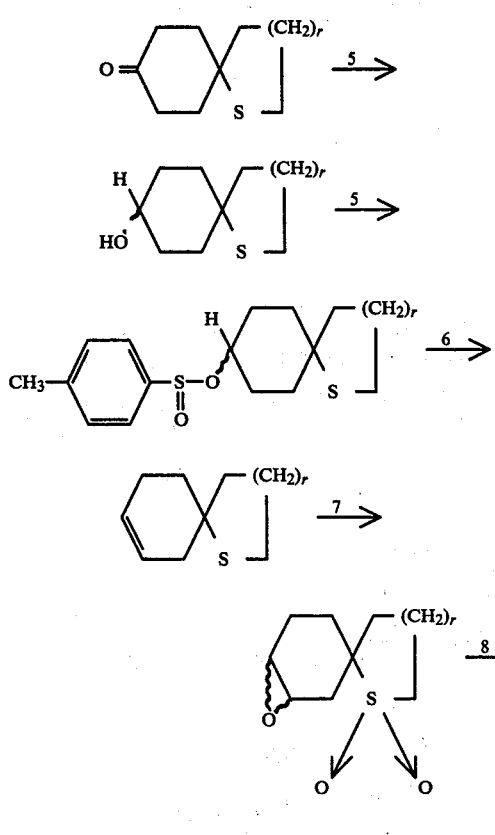
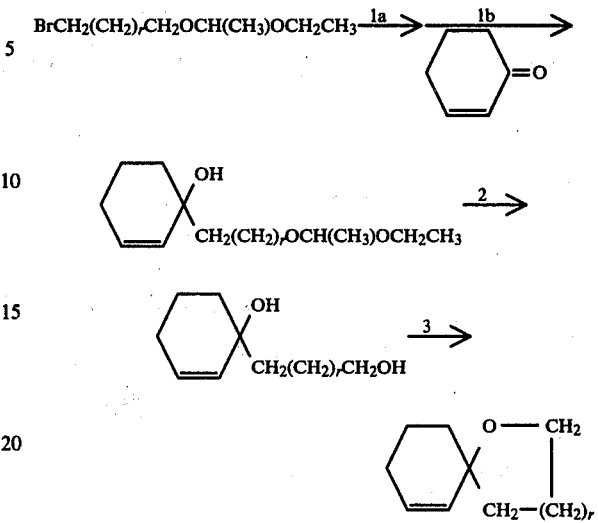
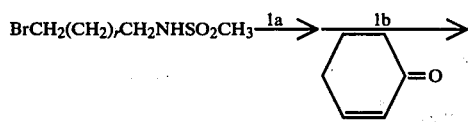
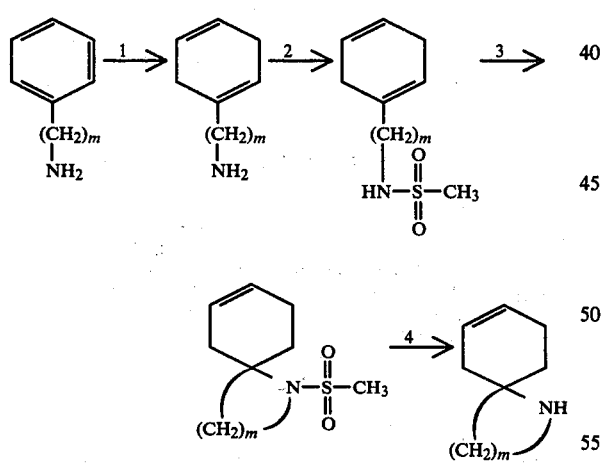
SCHEME VI
SCHEME IX
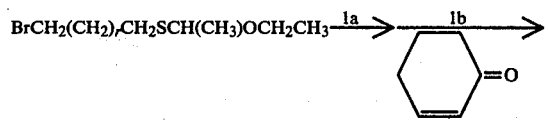
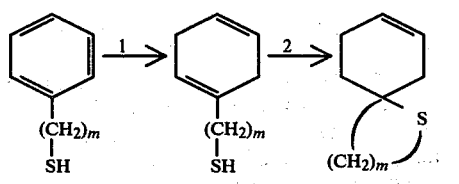
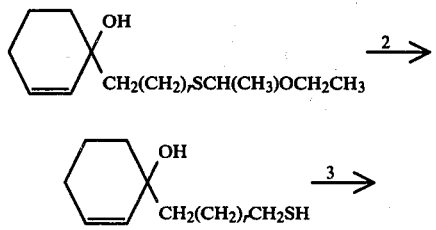

-continued
SCHEME IX

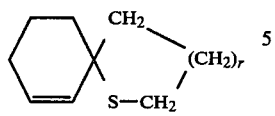

SCHEME X
Intermediates for compounds wherein Z is oxygen
and p + n + 3 is equal to 5 or 7; (j + k = 2 or 4)

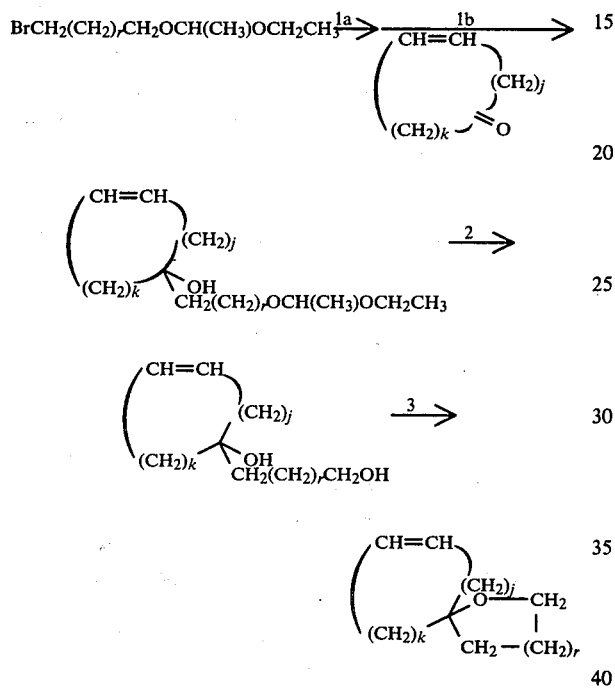

SCHEME XI
Intermediates for compounds wherein Z is NR3 and
p + n + 3 is equal to 5 or 7; (j + k = 2 or 4)

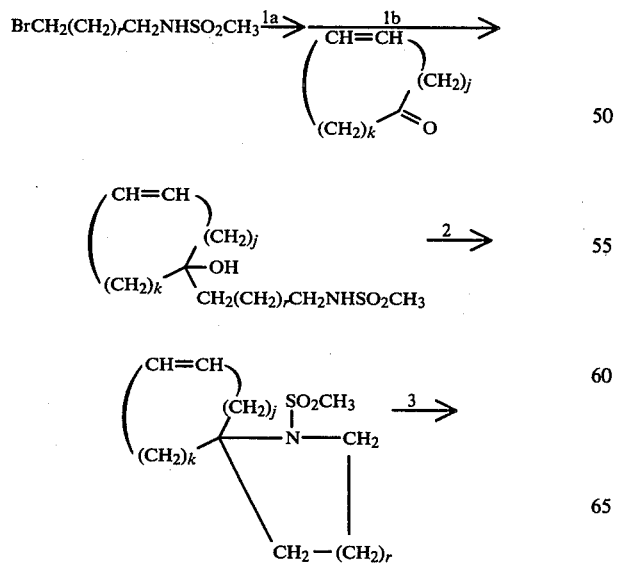

-continued
SCHEME XI
Intermediates for compounds wherein Z is NR3 and
p + n + 3 is equal to 5 or 7; (j + k = 2 or 4)

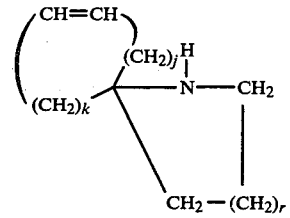

SCHEME XII
Intermediates for compounds wherein Z is S, SO, SO2
and p + n + 3 is equal to 5 or 7; (j + k = 2 or 4)

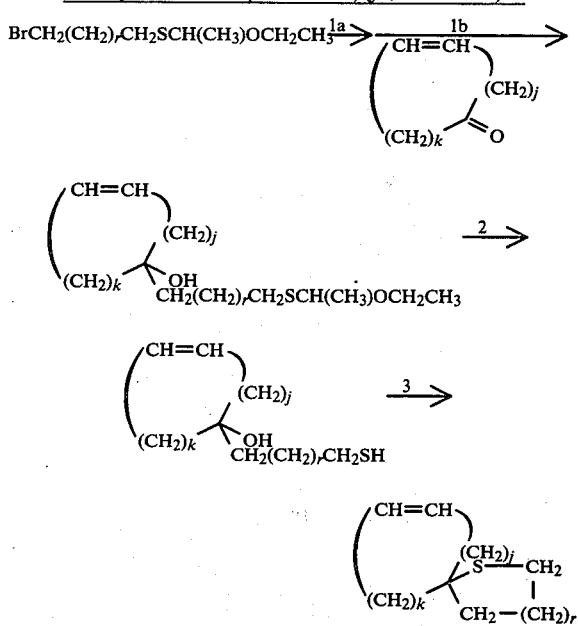

I claim:
1. A compound of the formula

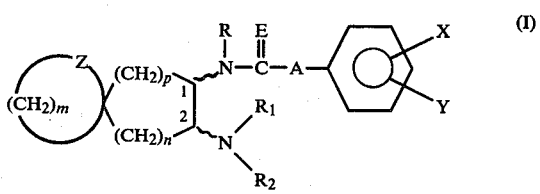

wherein
p is a whole number integer 0, 1 or 2 and n is a whole number integer 1, 2, or 3, so that the resulting cycloaliphatic ring containing them has six (6) carbon atoms;
m is 3 or 4;
A is a single chemical bond (—), —$(CH_2)_q$ where q is a whole number integer 0 to 4 or —$CH(CH_3)$—;
X and Y are independently selected from the group consisting of hydrogen, a halogen having an atomic number of from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxyacylamino (—NHC(=O)R$_4$ where R$_4$ is hydrogen or C$_1$ to C$_2$-alkyl);
R is hydrogen or C$_1$ to C$_3$-alkyl;
R$_1$ and R$_2$, taken separately, are each hydrogen, C$_1$ to C$_3$-alkyl or allyl;
R$_1$ and R$_2$, taken together with the nitrogen to which they are bonded complete a ring selected from the group consisting of azetidinyl, pyrrolidinyl and piperidinyl;
E is oxygen or sulfur;
Z is selected from the group consisting of oxygen, bivalent sulfur and sulfinyl;
provided that when p is 2, n is 1, m is 3, A is —(CH$_2$)$_q$ where q is 1, R is methyl, R$_1$ and R$_2$ are taken together with the nitrogen to which they are bonded to complete a pyrrolidinyl ring, E is oxygen, Z is oxygen, and the relative stereochemistry is (5α,7α,8β), then X and Y taken together on the phenyl ring cannot be chlorine on the 2- and 4-positions of the phenyl ring, or a pharmacologically acceptable salt thereof.

2. A compound according to claim 1 wherein
p is 1 or 2, n is 1 or 2;
m is 3 or 4;
A is —(CH$_2$)$_q$ where q is a whole number integer of from 0 to 1;
X and Y are independently hydrogen or a halogen having an atomic number of from 9 to 35;
R is C$_1$ to C$_3$-alkyl;
R$_1$ and R$_2$ are taken together with the nitrogen to which they are bonded to complete a ring selected from the group consisting of azetidinyl, pyrrolidinyl and piperidinyl;
E is oxygen;
Z is oxygen,
or a pharmacologically acceptable salt thereof.

3. A compound according to claim 2 which is 3,4-dichloro-N-methyl-N-[7-(1-pyrrolidinyl)-1-oxaspiro[4.5]dec-8-yl]benzeneacetamide, or a pharmacologically acceptable salt thereof.

4. A compound according to claim 2 wherein the compound is 4-bromo-N-methyl-N-[7-(1-pyrrolidinyl)-1-oxaspiro[4.5]dec-8-yl]benzamide, or a pharmacologically acceptable salt thereof.

5. A compound according to claim 2 which is 3,4-dichloro-N-methyl-N-[8-(1-pyrrolidinyl)-1-oxaspiro[4.5]dec-7-yl]benzeneacetamide, or a pharmacologically acceptable salt thereof.

6. A compound according to claim 2 wherein the compound is (+)-3,4-dichloro-N-methyl-N-[7-(1-pyrrolidinyl)-1-oxaspiro[4.5]dec-8-yl]benzeneacetamide, or a pharmacologically acceptable salt thereof.

7. A compound according to claim 2 where the compund is (−)-3,4-dichloro-N-methyl-N-[7-(1-pyrrolidinyl)-1-oxaspiro[4.5]dec-8-yl]benzeneacetamide, or a pharmacologically acceptable salt thereof.

8. A compound according to claim 1 wherein p is 0;
n is 3; m is 3 or 4;
A is —(CH$_2$)$_q$ where q is a whole number integer of from 0 to 4;
X and Y are independently hydrogen or a halogen having an atomic number of from 9 to 35;
R is C$_1$ to C$_3$-alkyl;
R$_1$ and R$_2$ are taken together with the nitrogen to which they are bonded to complete a ring selected from the group consisting of azetidinyl, pyrrolidinyl and piperidinyl;
E is oxygen;
Z is oxygen;
or a pharmacologically acceptable salt thereof.

9. A compound according to claim 8 wherein the compound is 3,4-dichloro-N-methyl-N-[7-(1-pyrrolidinyl)-1-oxaspiro[4.5]dec-6-yl]benzeneacetamide or a pharmacologically acceptable salt thereof.

10. A compound according to claim 2 wherein the compound is 1-N-methyl-N-[7-(1-pyrrolidinyl)-1-oxaspiro[4.5]dec-8-yl]benzeneacetamide, or a pharmacologically acceptable salt thereof.

11. A compound according to claim 2 wherein the compound is 4-chloro-N-methyl-N-[7-(1-pyrrolidinyl)-1-oxaspiro[4.5]dec-8-yl]benzeneacetamide.

12. A compound according to claim 2 wherein the compound is 4-bromo-N-methyl-N-[7-(1-pyrrolidinyl)-1-oxaspiro[4.5]dec-8-yl]benzeneacetamide, or a pharmacologically acceptable salt thereof.

13. A compound according to claim 1 wherein p is 1 or 2; n is 1 or 2; m is 3 or 4;
A is —(CH$_2$)$_q$ where q is a whole number integer of from 1 to 4;
X and Y are independently selected from the group consisting of hydrogen and methoxy
R is C$_1$ to C$_3$-alkyl;
R$_1$ and R$_2$ are taken together with the nitrogen to which they are bonded to complete a ring selected from the group consisting of azetidinyl, pyrrolidinyl and piperidinyl,
E is oxygen;
Z is oxygen,
or a pharmacologically acceptable salt thereof.

14. A compound according to claim 13 where the compound is 4-methoxy-N-methyl-N-[7-(1-pyrrolidinyl)-1-oxaspiro[4.5]dec-8-yl]benzeneacetamide, or a pharmacologically acceptable salt thereof.

15. A compound according to claim 1 wherein p is 1 or 2; n is 1 or 2; m is 3;
A is —(CH$_2$)$_q$—where q is a whole number integer of from 1 to 4;
X and Y are independently selected from the group consisting of hydrogen and C$_1$ to C$_3$-alkyl;
R is C$_1$ to C$_3$-alkyl;
R$_1$ and R$_2$ are taken together with the nitrogen to which they are bonded to complete a ring selected from the group consisting of azetidinyl, pyrrolidinyl, and piperidinyl;
E is oxygen;
Z is oxygen;
or a pharmacologically acceptable salt thereof.

16. A compound according to claim 15 wherein the compound is 4, N-dimethyl-N-[7-(1-pyrrolidinyl)-1-oxaspiro[4.5]dec-8-yl]benzeneacetamide.

17. A composition useful in pharmaceutically effective dosage unit form for alleviating pain in warm blooded animals which comprises a compound of claim 1 in combination with a pharmaceutically acceptable carrier.

18. A composition of claim 17 wherein the compound of claim 1 is a compound of the formula

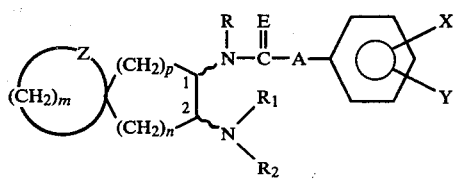

wherein p is 1 or 2, n is 1 or 2;

m is 3 or 4;

A is —$(CH_2)_q$ where q is a whole number integer of from 0 to 1;

X and Y are independently hydrogen or a halogen having an atomic number of from 9 to 35;

R is $C_1$ to $C_3$-alkyl;

$R_1$ and $R_2$ are taken together with the nitrogen to which they are bonded to complete a ring selected from the group consisting of azetidinyl, pyrrolidinyl and piperidinyl;

E is oxygen;

Z is oxygen;

or a pharmacologically acceptable salt thereof.

19. A composition of claim 1 wherein the compound of claim 1 is 3,4-dichloro-N-methyl-N-[7-(1-pyrrolidinyl-1-oxaspiro[4,5]dec-8-yl]benzeneacetamide, or a pharmacologically acceptable salt thereof.

20. A method for alleviating pain in a warm blooded animal which comprises administering to an animal suffering pain an effective amount of a compound of claim 1 in a pharmaceutically dosage unit form.

21. A method according to claim 20 wherein the compound of claim 1 is a compound of claim 3.

22. A compound of the formula

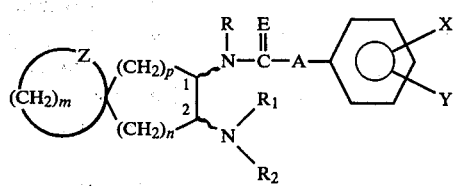

wherein p is a whole number integer 0, 1, 2, 3 or 4 and n is a whole number integer 0, 1, 2, 3 or 4, so that the resulting cycloaliphatic ring containing them has 5, 6 or 7 carbon atoms;

m is 3 or 4;

A is a single chemical bond (—), —$(CH_2)_q$ where q is a whole number integer 1 to 4 or —$CH(CH_3)$—;

X and Y are independently selected from the group consisting of hydrogen, a halogen having an atomic number of from 9 to 35, trifluoromethyl, nitro, methoxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxyacylamino (—NHC(=O)$R_4$ where $R_4$ is hydrogen or $C_1$ to $C_2$-alkyl);

R is hydrogen or $C_1$ to $C_3$-alkyl;

$R_1$ and $R_2$, taken separately, are each hydrogen, $C_1$ to $C_3$-alkyl or allyl;

$R_1$ and $R_2$, taken together with the nitrogen to which they are bonded complete a ring selected from the group consisting of azetidinyl, pyrrolidinyl, piperidinyl, pyrrolyl, 3-pyrrolinyl, 3-azabicyclo[3.1.0]-hexan-3-yl and 3-azabicyclo[3.2.0]heptan-3-yl;

E is oxygen or sulfur;

Z is selected from the group consisting of oxygen, bivalent sulfur, and sulfinyl;

provided that when p is 2, n is 1, m is 3, A is —$(CH_2)_q$ where q is 1, R is methyl, $R_1$ and $R_2$ are taken together with the nitrogen to which they are bonded to complete a pyrrolidinyl ring, E is oxygen, Z is oxygen, and the relative stereochemistry (5α,7α,8β), then X and Y taken together on the phenyl ring cannot be chlorine on the 2-and 4-positions of the phenyl ring;

or a pharmacologically acceptable salt thereof.

23. A compound according to claim 3 which is (5α,7α,8β)-(±)-3,4-dichloro-N-methyl-N-[7-(1-pyrrolidinyl)-1-oxaspiro[4.5]dec-8-yl]benzeneacetamide methanesulfonate.

24. A compound selected from the group consisting of (±)-(5α,7α,8β)-N-methyl-N-[7-(1-pyrrolidinyl)-1-oxaspiro[4.5]dec-8-yl]benzenepropanamide, (±)-(5α,7α,8β)-N-methyl-N-[7-(1-pyrrolidinyl)-1-oxaspiro[4.5]dec-8-yl]benzenebutanamide, (±)-(5ξ,7α,8β)-3,4-dichloro-N-methyl-N-[7-(1-pyrrolidinyl)-1-thiaspiro[4.5]dec-8-yl]benzeneacetamide, (±)-(5ξ-7α,8β)-4-bromo-N-methyl-N-[7-(1-pyrrolidinyl)-1-thiaspiro[4.5]dec-8-yl]benzamide, (±)-(5ξ-7α,8β)-3,4-dichloro-N-methyl-N-[8-(1-pyrrolidinyl)-1-thiaspirot[4.5]dec-7-yl]benzeneacetamide, and (±)-(5ξ-7α,8β)-4-bromo-N-methyl-N-[8-(1-pyrrolidinyl)-1-thiaspiro[4.5]dec-7-yl]benzamide, or a pharmacologically acceptable salt thereof.

25. A composition useful in pharmaceutically effective dosage unit form for alleviating pain in warm-blooded animals which comprises a compound of claim 22 in combination with a pharmaceutically acceptable carrier.

26. A method for alleviating pain in a warm-blooded animal which comprises administering to an animal suffering pain an effective amount of a compound of claim 22 in a pharmaceutically acceptable dosage unit form.

* * * * *

UNITED STATES PATENT OFFICE
CERTIFICATE OF CORRECTION

Patent No. 4,438,130                          Dated March 20, 1984

Inventor(s) Lester J. Kaplan

It is certified that error appears in the above-identified patent and that said Letters Patent are hereby corrected as shown below:

Column 22, line 34: "-benzene benzene mixture to" should read -- -benzene mixture to --.

Column 26, line 45: "slower moxing as" should read -- slower moving as --.

Column 27, line 5: "-[5ξ,6α,7β-1-[6-[methyl(phenylmetyl)-" should read -- (5ξ,6α,7β-1-[6-[methylphenylmethyl)-".

Column 29, line 45: Calculations for the "Found" line have been omitted. Should read: -- Found: C, 62.02; H, 7.17; N, 6.64; Cl, 16.60% --.

Column 30, line 29: "ammonia flask was" should read: -- ammonia (flask was--.

Column 38, line 41: "three nesk flask" should read: -- three neck flask --.

Column 41, lines 57-58: "(in the generic compound per se Formula (I)" should read: -- (in the generic compound per se Formula I) --.

Column 44, line 44: "and as asymmetric" should read -- and an asymmetric --.

Column 49, line 6, Scheme IV: formula reduction to 4 has been incorrectly typed as "5" and should read -- 4 --.

UNITED STATES PATENT OFFICE

CERTIFICATE OF CORRECTION

Patent No. 4,438,130    Dated March 20, 1984

Inventor(s) Lester J. Kaplan

It is certified that error appears in the above-identified patent and that said Letters Patent are hereby corrected as shown below:

Abstract, second line after Formula (I): "-(5α,7α,9β)-3,4-" should read -- (5α,7α,8β)-3,4- --.

Signed and Sealed this

Twentieth Day of November 1984

[SEAL]

Attest:

GERALD J. MOSSINGHOFF

Attesting Officer    Commissioner of Patents and Trademarks